United States Patent
Yokota

(10) Patent No.: US 6,945,930 B2
(45) Date of Patent: Sep. 20, 2005

(54) ENVIRONMENT ADAPTABLE MEASUREMENT ENDOSCOPE

(75) Inventor: Masayoshi Yokota, Hino (JP)

(73) Assignee: Olympus Corporation (JP)

( * ) Notice: Subject to any disclaimer, the term of this patent is extended or adjusted under 35 U.S.C. 154(b) by 81 days.

(21) Appl. No.: 10/232,422

(22) Filed: Aug. 27, 2002

(65) Prior Publication Data

US 2003/0060681 A1 Mar. 27, 2003

(30) Foreign Application Priority Data

Aug. 31, 2001 (JP) ......................................... 2001-264847
Aug. 31, 2001 (JP) ......................................... 2001-264849

(51) Int. Cl.$^7$ ............................. A61B 1/05; H04N 7/18
(52) U.S. Cl. ........................ 600/118; 600/109; 600/117; 600/175; 348/75
(58) Field of Search ................................ 600/101, 109, 600/117, 118, 129, 175; 348/45, 65, 72, 75, 76

(56) References Cited

U.S. PATENT DOCUMENTS

| | | | | |
|---|---|---|---|---|
| 5,860,912 A | * | 1/1999 | Chiba | 600/111 |
| 6,063,023 A | | 5/2000 | Sakiyama et al. | 600/118 |
| 6,517,478 B2 | * | 2/2003 | Khadem | 600/117 |
| 2002/0161284 A1 | * | 10/2002 | Tanaka | 600/176 |
| 2002/0183590 A1 | * | 12/2002 | Ogawa | 600/117 |
| 2002/0196334 A1 | * | 12/2002 | Saito et al. | 348/65 |
| 2004/0019255 A1 | * | 1/2004 | Sakiyama | 600/175 |

FOREIGN PATENT DOCUMENTS

JP     2001-275934     10/2001

* cited by examiner

Primary Examiner—John P. Leubecker
(74) Attorney, Agent, or Firm—Ostrolenk, Faber, Gerb & Soffen, LLP

(57) ABSTRACT

A measurement endoscope system includes: an image pickup device, an endoscope insertion portion to which a plurality of stereo measurement optical adaptors and a normal measurement adaptor are detachably attachable, a control unit for accommodating the endoscope insertion portion, a face mounted display for stereoscopically viewing a normal endoscope image or stereoscopically viewing the endoscope image as a pseudo stereo image, and the like. The control unit includes a CPU for controlling the execution of various functions based on a main program, a ROM, a RAM, a PC card, a USB port, an RS-232 port, an audio signal processing circuit, and a video signal processing circuit. The control unit can be connected externally to a PC. The measurement endoscope system allows taking image re-measurements under a correct measurement environment simple operation, with the re-measurements being performed promptly without consideration of the measurement environment. Thus, the operability of the system is improved and greatly expedited.

22 Claims, 21 Drawing Sheets

400; # ENVIRONMENT ADAPTABLE MEASUREMENT ENDOSCOPE

RELATED APPLICATIONS

This application claims benefit of Japanese Applications No. 2001-264847 filed in Japan on Aug. 31, 2001 and 2001-264849 filed in Japan on Aug. 31, 2001, the contents of which are incorporated by this reference.

FIELD OF THE INVENTION

The present invention relates to an endoscope for forming two images of a subject on an image pick-up device of an endoscope main body via a pair of objective lenses at different positions, and for performing the measurement or examination by image processing using the obtained endoscope images. The invention further relates to a measurement processing method (measurement software) for handling a measurement image recorded by the above-mentioned endoscope apparatus on a personal computer (hereinafter, referred to as a PC).

BACKGROUND INFORMATION

In general, detailed examination of a subject using an endoscope requires setting up the subject for being examined. To satisfy this requirement, conventionally, various measuring means for measuring of the subject using the endoscope have been proposed and disclosed.

For example, a proposal disclosed in U.S. Pat. No. 6,063,023 shows an endoscope that is instrumented for stereo measurements. Japanese Unexamined Patent Application Publication No. 2001-275934, also provided by the applicant of the present invention, shows an endoscope which automatically selects and executes measurement methods depending on the type of optical adaptor.

In the endoscope apparatus disclosed in U.S. Pat. No. 6,063,023, an optical adaptor having two optical systems necessary for image pick-up and measurement of a subject in an endoscope main body are disclosed. Images through two lens systems in the optical adaptor are formed on a single image pickup device. The measurement is performed by image processing using at least the obtained endoscope images. The endoscope comprises measurement processing means to perform various functions. For example, the measurement processing means performs processing for reading information from a recording medium on which the optical data from the optical adaptor is recorded. The measurement processing means also performs processing for correcting the optical data based on the position error of an image pick-up system of the endoscope main body. The measurement processing means also performs processing for coordinate-transforming the image for measurement based on the corrected optical data. The measurement processing means also performs processing for obtaining a three-dimensional coordinate at an arbitrary point by matching the two images based on the two coordinate-transformed images.

In the endoscope having the above-mentioned structure, the three-dimensional coordinate is obtained at an arbitrary point on the subject by matching two images based on two pieces of image information obtained by coordinate-transforming two images of the subject captured by the image pick-up device via the optical adaptor. Consequently, the endoscope may be designed at low cost and with excellent measurement accuracy.

Japanese Unexamined Patent Application Publication No. 2001275934 discloses an endoscope comprising a connecting portion provided for at an endoscope tip portion, and a plurality of optical adaptor types detachably coupleable to the connecting portion, for forming a subject image to an image pick-up device. This device performs the measuring by connecting one type of optical adaptor and imaging an image signal obtained by the image pick-up device. The endoscope further comprises measurement processing means that performs menu display processing for selection based on display data previously associated with the plurality of optical adaptors and performs measurement processing based on the selected result in the menu display processing.

In the endoscope having the above-mentioned structure, the optical adaptor is selected on the menu, thereby automatically selecting a measuring method corresponding to the selected optical adaptor. The measurement processing can be executed corresponding to the selected measuring method only by pressing an executing switch provided for an endoscope operating portion, in the case of executing the measurement.

Japanese Unexamined Patent Application Publication No. 2001275934 discloses an embodiment, in which images of the plurality of optical adaptors are calibrated. The resultant images are stored as data on a measurement environment in a compact flash memory card utilized as an external storage medium. By selecting the proper optical adaptor used on the menu, the data on the environment is used corresponding to the selected optical adaptor.

In general, characteristics of a photographing state of the image to be measured are varied depending on the type of a camera control unit (hereinafter, referred to as a CCU) for converting signals outputted from a video endoscope main body, an optical adaptor for measuring having an objective lens and a video endoscope into TV signals or the type of recording mediums for converting the TV signal into a digital signal and recording it, or the difference of devices. Therefore, the accurate measurement can be performed by various correction so that the measuring endoscope is set to match the combination of the devices upon photographing the measured image. That is, in all cases, elaborate and time-consuming steps involving the measuring settings or parameters are necessary.

Thus, it is important in the measurement apparatus or system to form data necessary for correcting the measurement image before processing for actually calculating a measuring value and this processing has characteristics depending on the device for recording the image. Since the above processing method is performed in the device for recording the image, the measuring can conventionally be executed only in the endoscope upon performing the measurement of the temporarily recorded image again. Alternatively, the measurement of the image recorded by one device can be performed on another device. However, the measurement can be performed again only on the measuring endoscope apparatus.

Recently, re-measurement is increasingly performed by using the measured image recorded by the combination of various devices (under the testing environments) in accordance with the increase in type of endoscope main bodies, optical adaptors, and CCUs to match the application of various measurements.

However, since the conventional apparatuses have no means for recording data indicating under which testing environment the image is photographed in the measured images, there is a danger that upon re-measurements using the same image for a while, the measurement environment cannot be set again or the measurement environment is set by erroneous connection of the devices for purpose of re-measurement because an operator forgets the measurement environment upon photographing the image.

The data on the measurement environment set to in the conventional apparatuses is limited to data on an arbitrary measurement environment and, therefore, when the re-measurement is performed by the image that is not suitable to the data on the measurement environment in the measurement endoscope apparatus such as a measurement image using the different type of optical adaptor, all the devices must be connected to the apparatus before actual re-measurement and the measurement environment must manually be performed again. Thus, the operation for re-measurement is excessively complicated and troublesome.

Further, when the above-mentioned apparatus disclosed in Japanese Unexamined Patent Application Publication No. 2001-275934 includes a facility for recording the photographed image to a detachable recording medium such as a floppy disk or a facility for capturing the image recorded on the recording medium to another measurement endoscope apparatus, it is necessary to set the endoscope, optical adaptor, or CCU which is actually used upon photographing the image to be actually connected to a measuring endoscope to be used for re-measurement on an endoscope different from the endoscope used for the actual image photographing.

Not only the recorded image is captured or displayed on the PC but also much PC software which can easily perform this operation is available.

Accordingly, various measured images can generally be managed on the above-mentioned PC software. However, since neither means nor processing for setting the testing environment on the PC exists, the re-measurement of the image captured to the PC cannot be performed.

SUMMARY OF THE INVENTION

Accordingly, it is one object of the present invention to provide an endoscope capable of preventing measurement under erroneous measurement environment assumptions, upon re-measurement using a recorded measurement image. Re-measurement is promptly performed without considering the measurement environment. Operability is improved by simply performing the re-measurement under the correct testing environment.

It is another object of the present invention to provide a measurement processing method (measurement software) capable of improving the operating efficiency of examination by re-measurement of the image recorded by the endoscope on a PC.

It is another object of the present invention to provide a measurement processing method capable of preventing measurement under an erroneous testing environment upon using a PC. In this manner, the measurement environment is suitably set to images recorded under various testing environments. Re-measurement is promptly performed without considering the environment. Operability is improved by simply performing the re-measurement under the correct testing environment.

The endoscope of the present invention comprises: a connecting portion provided for an endoscope tip portion; an optical adaptor detachably connected to the connecting portion, for coupling a subject image to image pick-up means; a signal processing unit for processing an image signal from the image pick-up means; recording means for recording an image processed by the signal processing unit; and test set-up means for performing measurement based on the image. The endoscope further comprises: test or measurement environment data recording means for recording first data on the environment as a pair of images recorded by the recording means; comparing means for comparing the first data on the measurement environment with second data on the environment which has already been recorded on the apparatus; and selecting means for selecting the first data on the test environment or the second data on the environment in accordance with information from the comparing means.

The invention is further directed to a measurement processing method performed by a PC for capturing (copying) an image recorded by an environment measurement apparatus that comprises: a connecting portion provided for an endoscope tip portion; an optical adaptors detachable to the connecting portion having an objective lens, for coupling two images to image pick-up means; processing for measurement of an image signal from the image pick-up means by imaging processing by connecting the optical adaptor; means for recording a measurement image, calibration data including optical characteristics of the optical adaptor or the like, as information necessary for setting the measurement environment; and means for copying the image recorded in the apparatus to a detachable recording medium together with the information on the measurement environment and the calibration data, comprises: a step of determining whether or not the information on the measurement environment matches the current setting of the measurement environment by referring to the information on the environment recorded to the measurement environment image; a step of automatically setting the environment by using the calibration data which is recorded to the image; a step of informing or indicating the fact that neither the information on the environment nor the calibration data is recorded to the environment image; a step of managing a plurality of types of the calibration data taken out from the image in the personal computer; a step of searching the same information on the measurement environment from the calibration data which has already been managed in the PC by referring to the information on the environment which is recorded to the environment image; a step of automatically forming the data on the environment which is used upon correcting the showing the measurement environment image by using the calibration data as the search result; a step of forming the data on the environment by using the data selected from pieces of the calibration data; a step of coordinate-transforming the image by using the data on the environment; a step of obtaining a three-dimensional coordinate at an arbitrary point by matching two images based the two coordinate-transformed images; and a step of calculating a measurement value such as a desired length from the three-dimensional coordinate.

Other features and benefits of the present invention will be obvious by the following description.

DETAILED DESCRIPTION OF THE PREFERRED EMBODIMENTS

Figure 1:
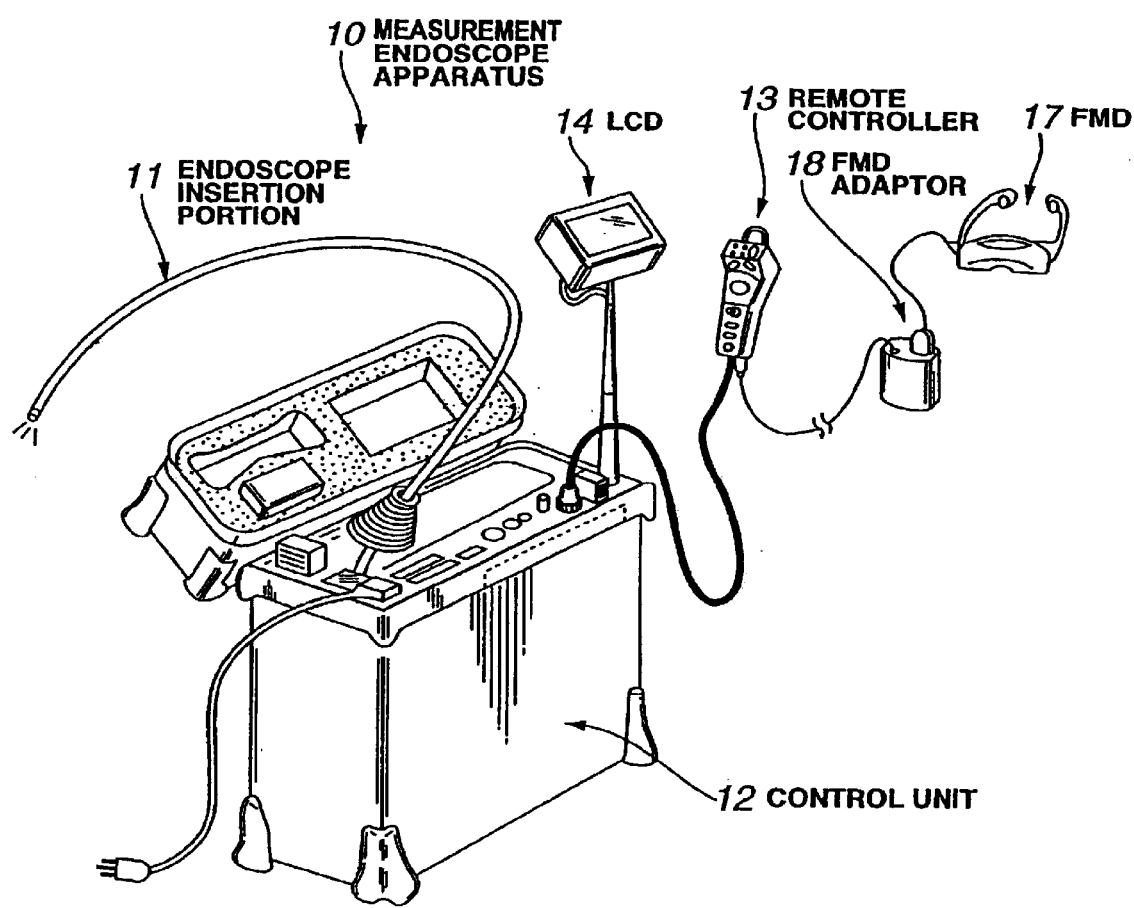
FIG. 1 is a perspective view showing the system structure of a measurement endoscope system according to a first embodiment of the present invention.
Figure 2:
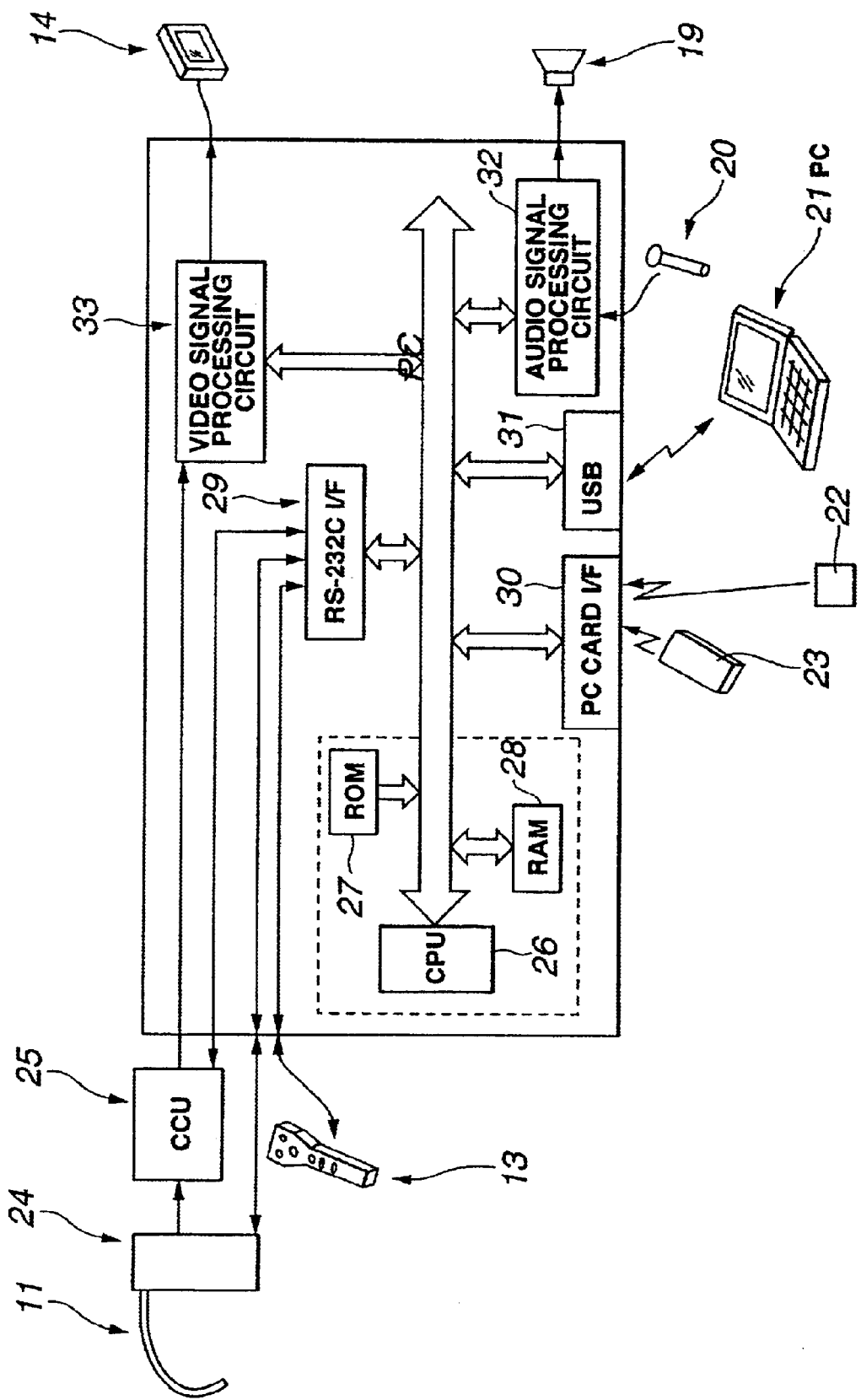
FIG. 2 is a block diagram showing the structure of circuits of the endoscope in FIG. 1.
Figure 3:
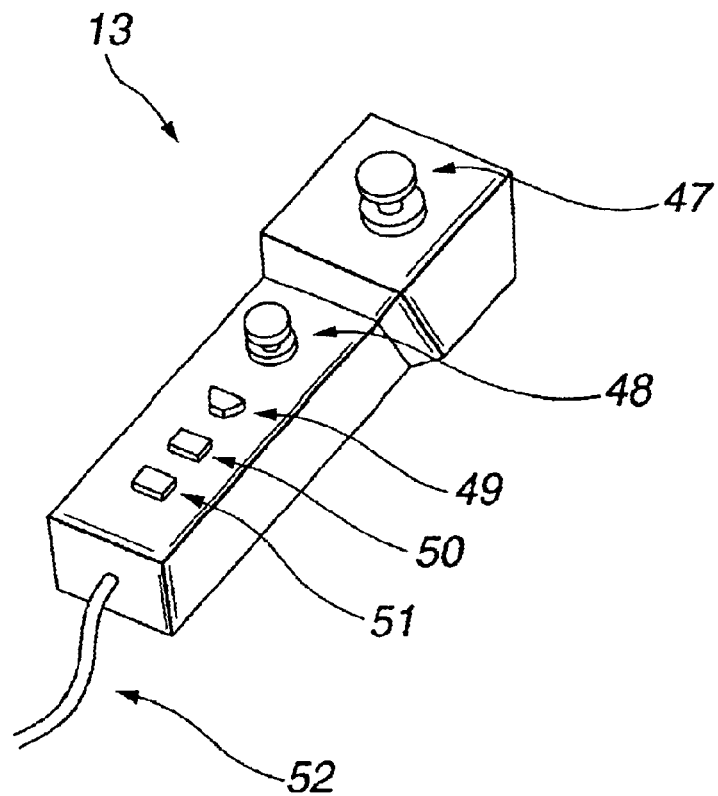
FIG. 3 is a perspective view showing the structure of a remote controller in FIG. 1.
Figure 4:
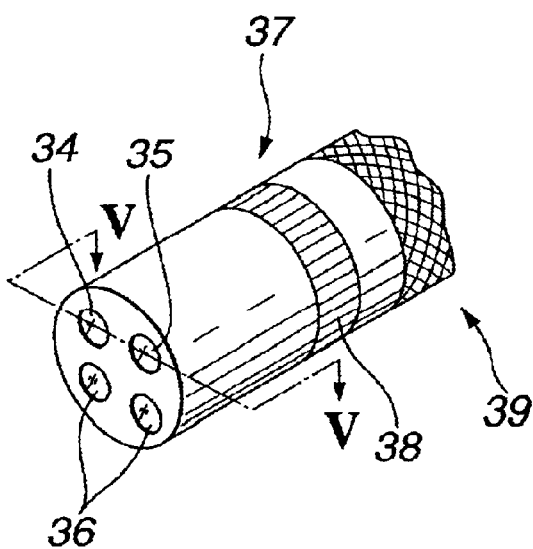
FIG. 4 is a perspective view showing the structure of an endoscope tip portion of an endoscope insertion portion in FIG. 1 to which a stereo measurement adaptor is attached.
Figure 5:
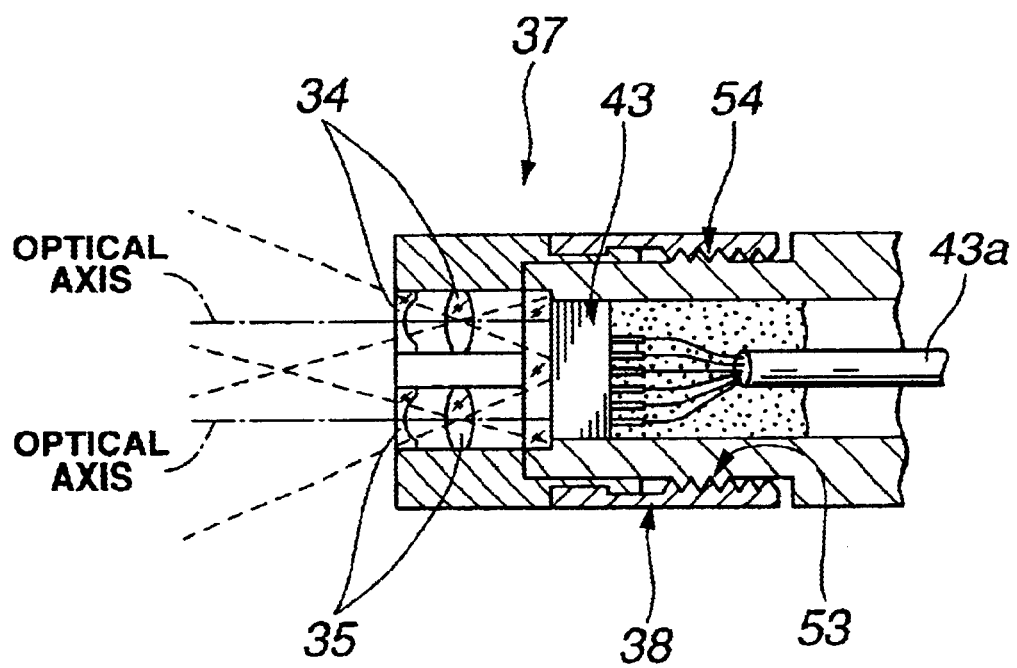
FIG. 5 is a cross-sectional view of a V—V cut-line in FIG. 4.
Figure 6:
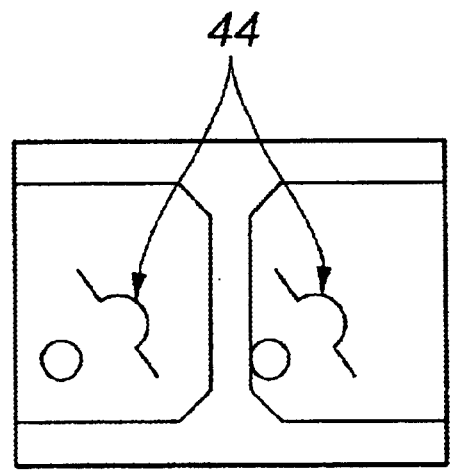
FIG. 6 is a diagram showing an endoscope image when attaching the stereo measurement adaptor in FIG. 4.
Figure 7:
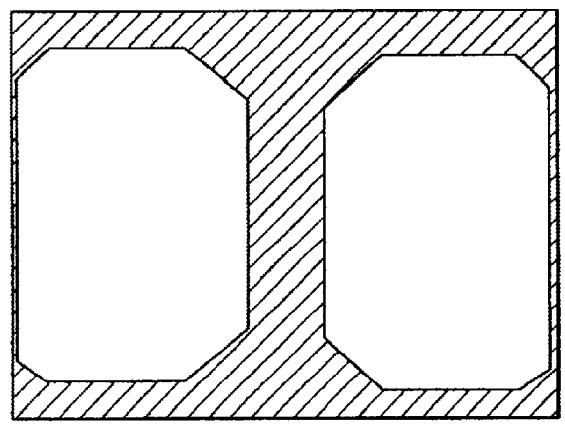
FIG. 7 is a diagram showing a mask-shaped image of the stereo measurement adaptor in FIG. 4.
Figure 8:
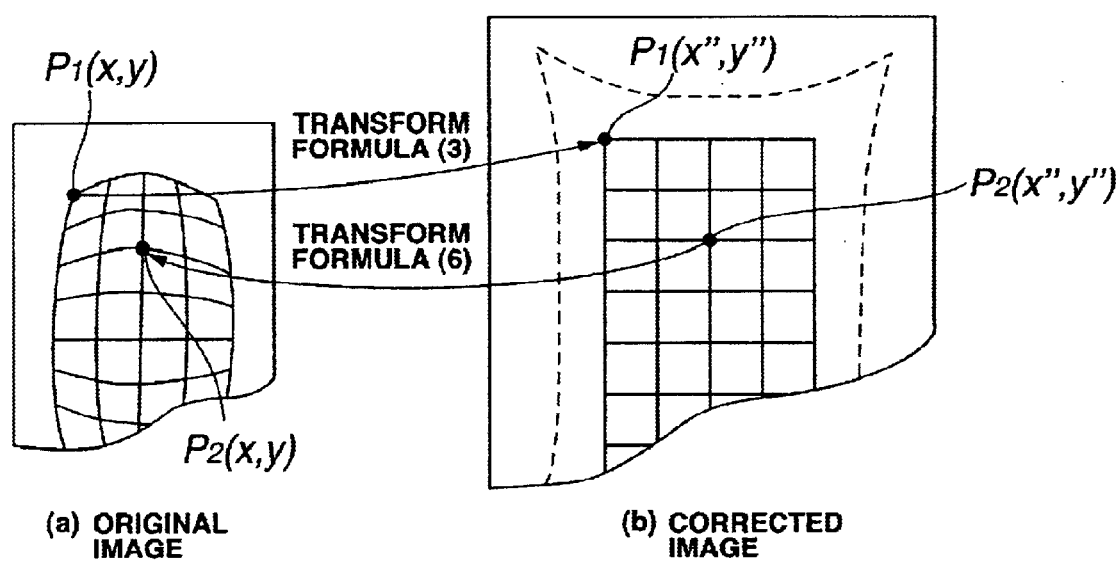
FIG. 8 is a diagram showing a relationship between an original image and a corrected image for explaining the setting of a measurement environment in the endoscope apparatus in FIG. 1.
Figure 9:
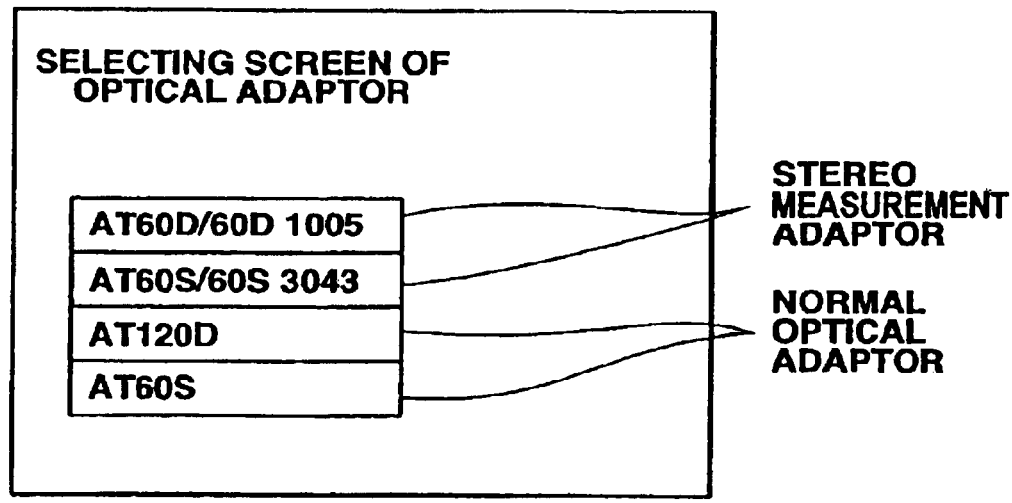
FIG. 9 is a diagram showing an example of a selecting screen of an optical adaptor displayed on an LCD in FIG. 1.
Figure 10:
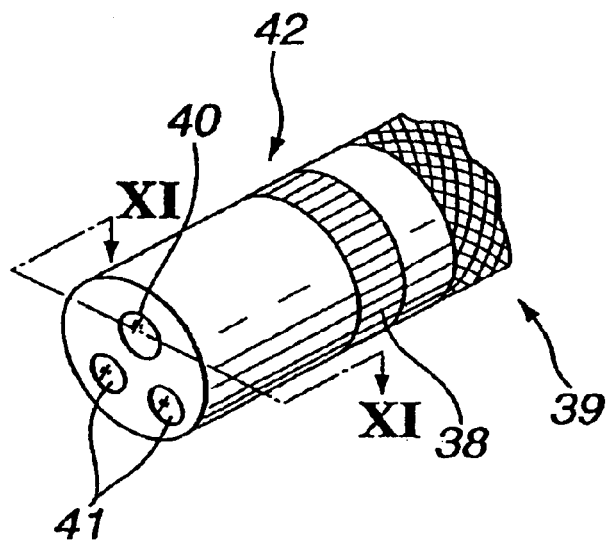
FIG. 10 is a perspective view showing the structure of the endoscope tip portion of the endoscope insertion portion in FIG. 1 to which a normal optical adaptor is attached.
Figure 11:
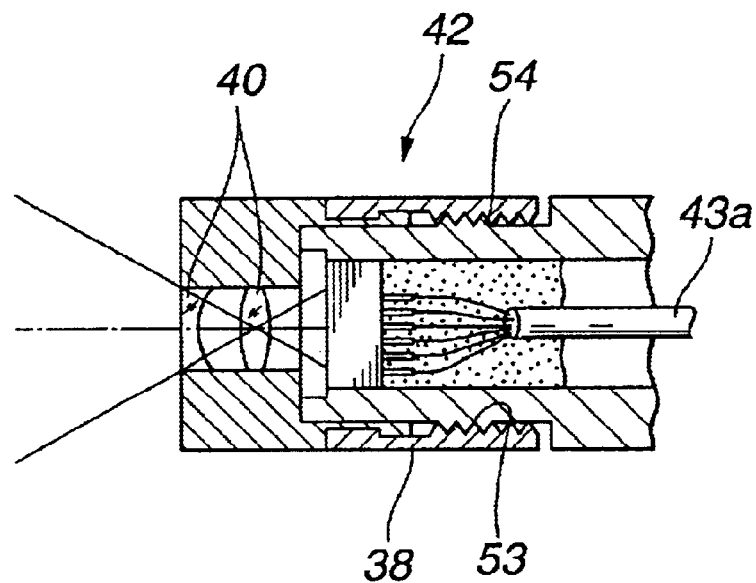
FIG. 11 is a cross-sectional view of a XI—XI cut line in FIG. 10.
Figure 12:
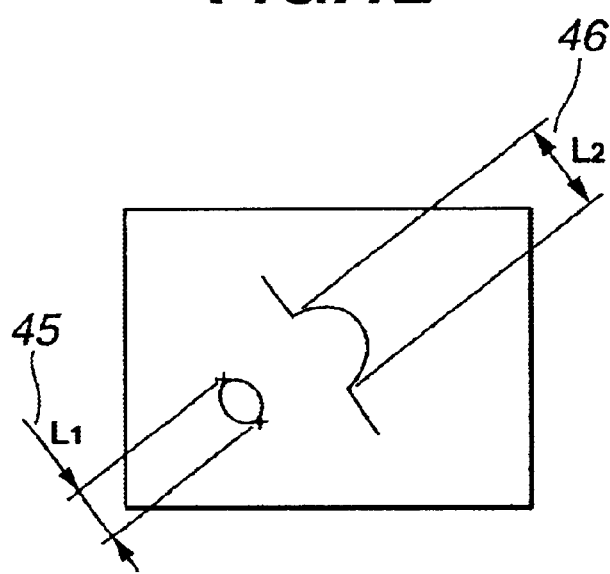
FIG. 12 is a diagram showing an endoscope image when attaching the normal optical adaptor in FIG. 10.
Figure 13:
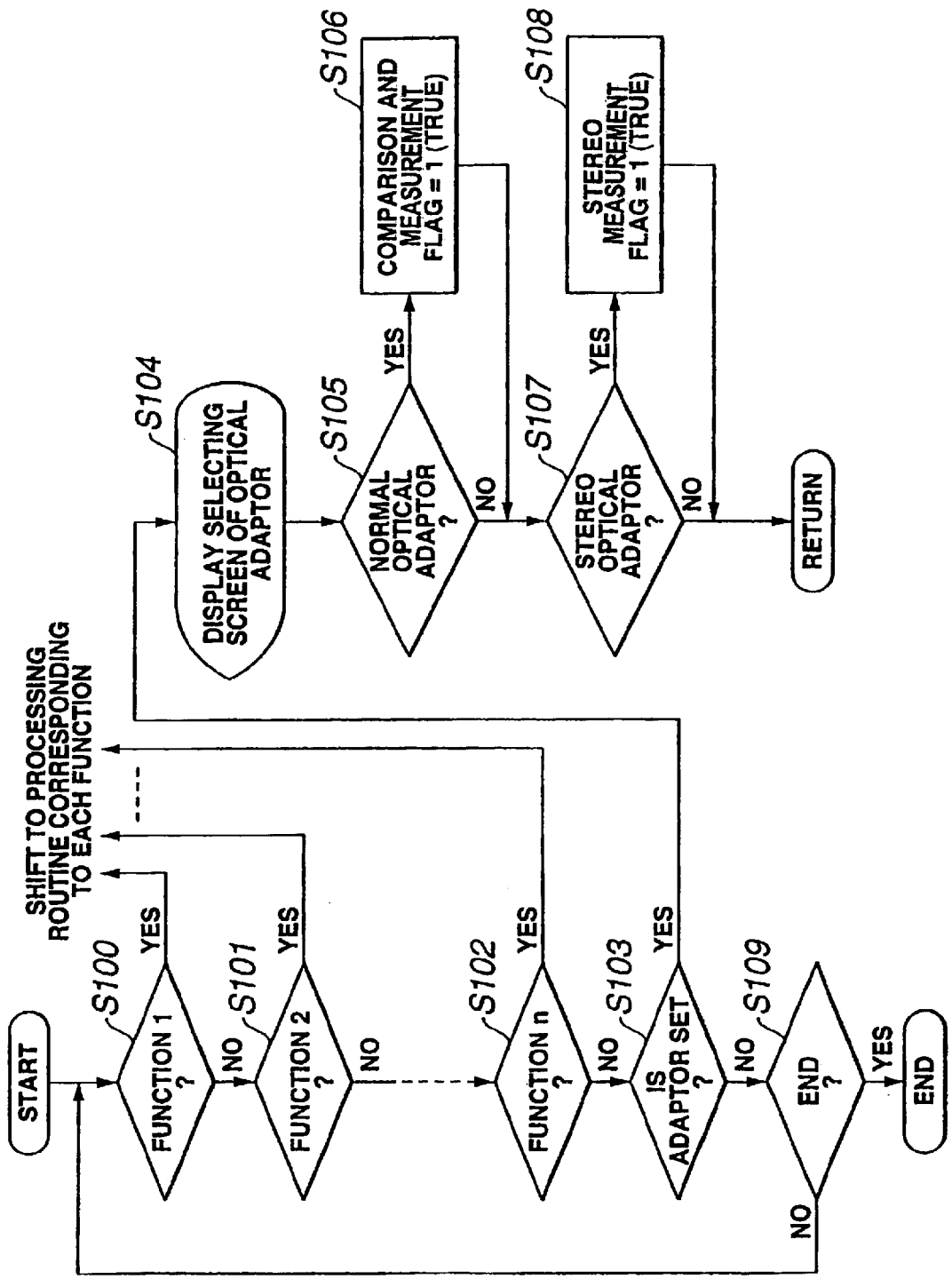
FIG. 13 is a first flowchart showing an example of control operation by a CPU in FIG. 2 as a feature.
Figure 14A:
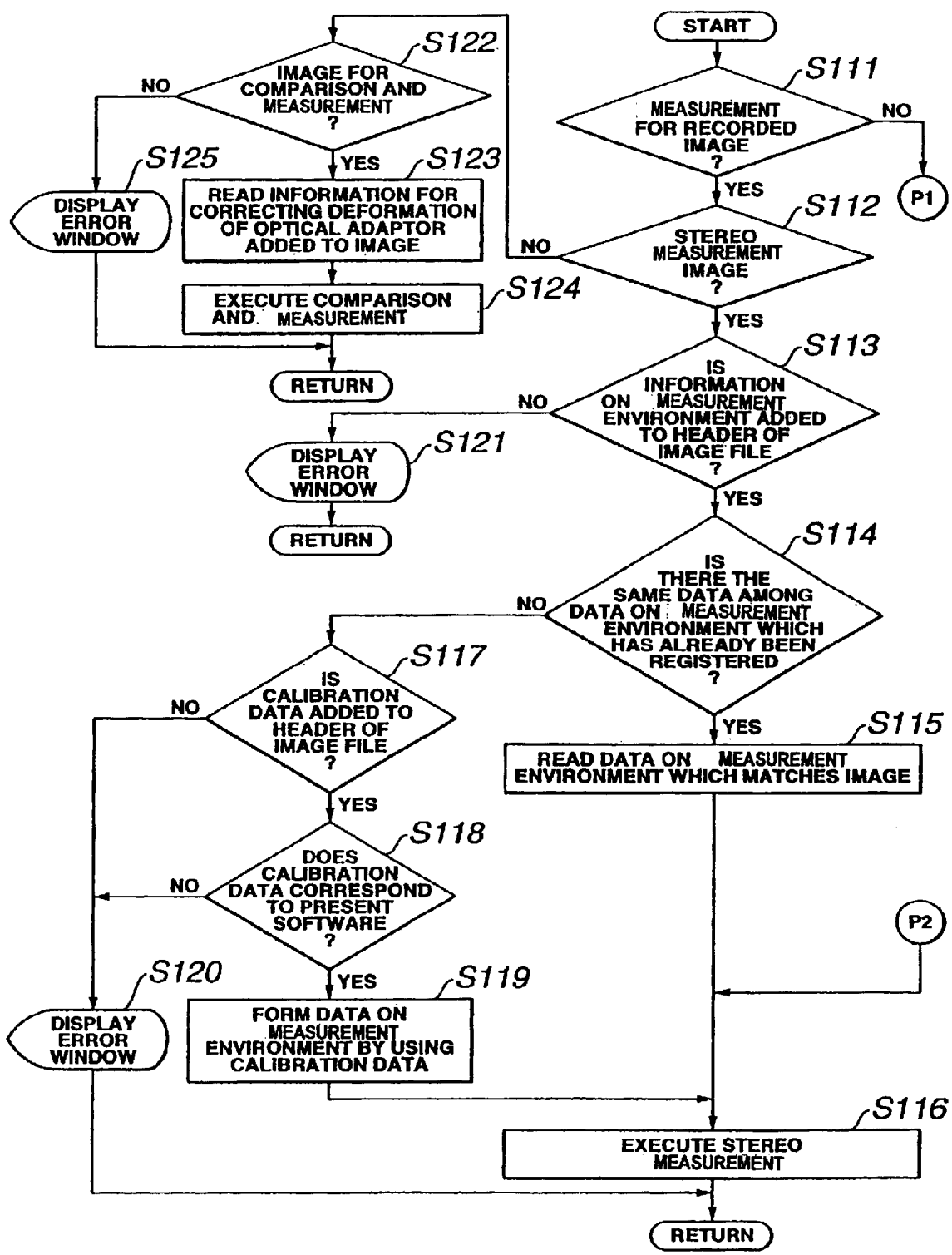
FIG. 14A is one part of a second flowchart showing the example of the control operation by the CPU in FIG. 2 as a feature.
Figure 14B:
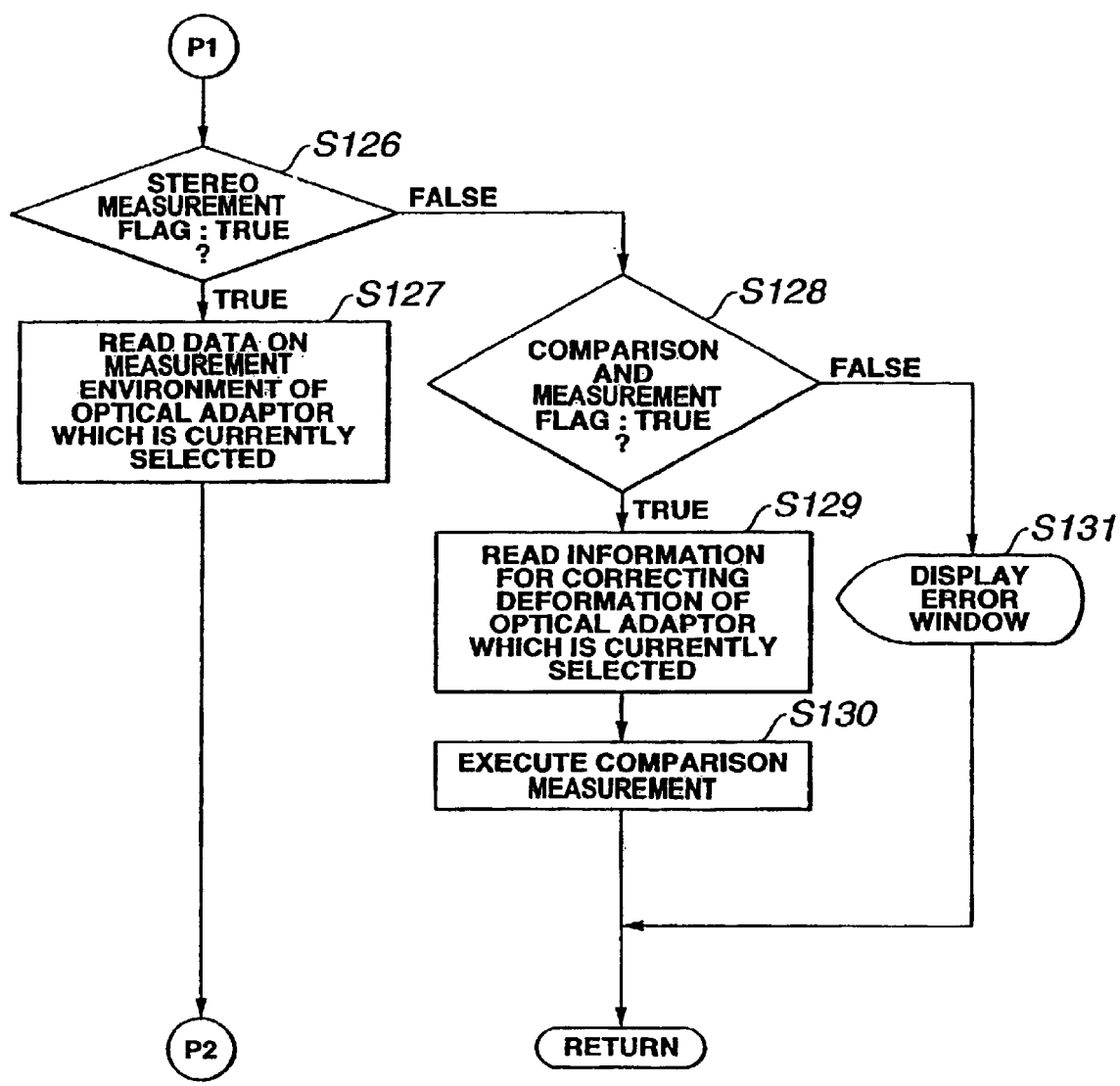
FIG. 14B is another part of the second flowchart showing the example of the control operation by the CPU in FIG. 2 as the feature.

FIGS. 1 to 14B relate to a first embodiment of the present invention. FIG. 1 is a perspective view showing the system structure of a measurement endoscope. FIG. 2 is a block diagram showing the structure of circuitry of the measurement endoscope apparatus illustrated in FIG. 1. FIG. 3 is a perspective view showing the structure of a remote controller illustrated in FIG. 1. FIG. 4 is a perspective view showing the structure of a tip portion of an endoscope insertion portion illustrated in FIG. 1. The tip portion is adapted to attach to a stereo measurement adaptor. FIG. 5 is a cross-sectional view of a V—V cut-line of the illustration of FIG. 4. FIG. 6 shows an endoscope image when attaching the stereo measurement adaptor illustrated in FIG. 4. FIG. 7 shows a mask-shaped image of the stereo measurement adaptor illustrated in FIG. 4. FIG. 8 shows a relationship between an original image and a corrected image for explaining the setting of a measurement environment in the endoscope illustrated in FIG. 1. FIG. 9 shows an exemplary selecting screen of an optical adaptor displayed on an LCD illustrated in FIG. 1. FIG. 10 is a perspective view showing the structure of a tip portion of the endoscope insertion portion illustrated in FIG. 1 to which a normal optical adaptor is attached. FIG. 11 is a cross-sectional view of a XI—XI cut line through the illustration of FIG. 10. FIG. 12 is a shows an endoscope image when attaching a normal optical adaptor illustrated in FIG. 10. FIGS. 13A and 13B are flowcharts showing an exemplary control operation performed by the CPU illustrated in FIG. 2. FIGS. 14A and 14B are second flowcharts showing an exemplary control operation performed by the CPU illustrated in FIG. 2.

The system structure of a measurement endoscope 10 will be described according to a first embodiment. Referring to FIG. 1, the measurement endoscope 10 comprises an endoscope insertion portion 11 which incorporates an image pick-up device and to which a plurality of optical adaptors for stereo measurement and an optical adaptor for normal measurement are detachably attached, a control unit 12 for accommodating the endoscope insertion portion 11, a remote controller 13 for performing various control operations of the system of the endoscope 10, a liquid crystal monitor (hereinafter, referred to as an LCD) 14 for displaying the endoscope image or the contents of the control operation (for example, a processing menu), a face mounted display (hereinafter, referred to as an FMD) 17 for stereoscopically viewing the normal endoscope image or an pseudo stereo image, and an FMD adaptor 18 for supplying image data to the FMD 17.

The system structure of the endoscope 10 will be described in detail with reference to FIG. 2. Referring to FIG. 2, the endoscope insertion portion 11 is connected to an endoscope unit 24. The endoscope unit 24 is arranged in, for example, the control unit 12 shown in FIG. 1. Further, the endoscope unit 24 comprises a light source device for providing illumination light necessary for photographing and an electric bending device for electrically bending the endoscope insertion portion 11 freely (not shown).

An image pick-up signal is produced from a solid image pickup device 43 (see FIG. 5) arranged at the insertion portion 11. The pick-up signal is inputted to a camera control unit (hereinafter, referred to as a CCU) 25. The CCU 25 converts the image pick-up signal into a video signal such as an NTSC signal, and supplies the converted signal to main processing circuits in the control unit 12.

Referring to FIG. 2, the control unit 12 includes a CPU 26 for controlling the execution and operation of various functions based on a main program, a ROM 27, a RAM 28, a PC card interface (hereinafter, referred to as a PC card I/F) 30, a USB interface (hereinafter, referred to as a USB I/F) 31, an RS-232C interface (hereinafter, referred to as an RS-232C I/F) 29, an audio signal processing circuit 32, and a video signal processing circuit 33.

The RS-232C I/F 29 is connected to the CCU 25, the endoscope unit 24, and the remote controller 13. The remote controller 13 controls and instructs the operation of the CCU 25 and the endoscope unit 24. The RS-232C I/F 29 performs communications necessary for controlling the operation of the CCU 25 and the endoscope unit 24 based on the operation of the remote controller 13.

The USB I/F 31 is an interface for electrically connecting the control unit 12 to a PC 21. When the control unit 12 and the personal computer 21 are connected via the USB I/F 31, various control instructions may be provided to the control unit 12 via PC 21. These instructions may include, for example, instructions for displaying the endoscope image and processing an image upon measurement thereof. Further, control information and data necessary for various processing can be received and transmitted between the control unit 12 and the PC 21.

A PCMCIA memory card 22 and a compact flash memory card 23 as a flash memory card may be detachably connected to the PC card I/F 30. When any of the above memory cards is attached, the control unit 12 can read data relating to control processing information or image information stored in the memory card. The control unit 12 may then capture the read data via PC card I/F 30. Alternatively, the control unit 12 may write data to the memory card relating to image information or control processing information. This write operation may be controlled by the CPU 26 via PC card I/F 30.

The video signal processing circuit 33 combines a video signal from the CCU 25 and a display signal based on an operation menu, generated under the control of the CPU 26. In this manner, a combined image is graphically displayed by combining the endoscope image supplied from the CCU 25 and the operation menu. Further, the video signal processing circuit 33 supplies a video signal, which is subjected to processing for displaying the data on the LCD 14. Thus, the combined image of the endoscope image and the operation menu is displayed on the LCD 14. The video signal processing circuit 33 can individually display an image of the endoscope image or the operation menu.

An audio signal is supplied to the audio signal processing circuit 32. The audio signal is collected and generated by a microphone 20 and recorded to a recording medium such as a memory card. Alternatively, the audio signal may be obtained by reading a signal stored on the recording medium, such as the memory card. The audio signal processing circuit 32 processes the audio signal to play the supplied signal (amplification). The audio signal processing circuit 32 outputs the audio signal to a speaker 19.

The CPU 26 executes programs stored in the ROM 27, and performs the control operation of the entire system by various circuit units so as to execute processing corresponding to various purposes.

Next, a description is given of the structure of the remote controller 13 and the example of the control operation of a program of the CPU 26 based on the operation of the remote controller 13 with reference to FIG. 3.

The remote controller 13 used for the endoscope 10 according to the first embodiment is improved for upgrading the operability upon various measurements.

Referring to FIG. 3, the remote controller 13 comprises a joy stick 47, a lever switch 48, a freeze switch 49, a store switch 50, and a measurement executing switch 51, which are provided together for at least an upper surface of a casing. The remote controller 13 is easily operated by a user.

In the remote controller 13, the joy stick 47 is a switch used to control a bending operation of the endoscope tip portion, and can freely instruct such an operation in any direction through an angle of 360°. The lever switch 48 is used to move a pointer to select various menu operations graphically displayed or to perform the measurement. The lever switch 48 has a similar shape to that of the joy stick 47. The freeze switch 49 is used to display a still image when displaying a moving picture of the endoscope displayed on the LCD 14. The store switch 50 is used to record the still image to the PCMCIA memory card 22 (refer to FIG. 2), for example, when displaying the still image by pressing the freeze switch 49. The measurement executing switch 51 is used to execute measurement software.

The freeze switch 49, the store switch 50, and the measurement executing switch 51 may be, for example, on/off type pressing switches. A function other than the above-mentioned functions can be allocated to the lever switch 48.

For example, an image zoom up function may be executed by laying the lever switch 48 to the right and an image zoom down function may be executed by laying the lever switch 48 to the left. These functions may be allocated to the lever switch 48. Upon measurement using a zoom image, the image may not correctly be measured because a zoom ratio of the image is changed. In this case, the CPU 26 receives an operation signal by pressing the measurement executing switch 51 and the control operation is performed so that the measurement is executed after the zoom function is promptly canceled and the image is frozen. The control operation may be performed so that the image can be measured without modification in consideration of the zoom ratio.

Next, a description is given of the structure of the stereo adaptor used for the endoscope 10 according to the first embodiment with reference to FIGS. 4 to 6.

FIGS. 4 and 5 show a stereo measurement adaptor 37 is attached to the endoscope tip portion 39. The stereo measurement adaptor 37 is fixed by being screwed to a male screw 54 of the endoscope tip portion 39 by using a female screw 53 of a fixing ring 38.

A pair of illumination lenses 36 and two objective lens systems 34 and 35 are mounted on the tip of the stereo optical adaptor 37. The two objective lenses 34 and 35 form two images on the image pick-up device 43 arranged in the endoscope tip portion 39. An image pick-up signal obtained by the image pickup device 43 is supplied to the CCU 25 via an electrically connected signal line 43a and the endoscope unit 24. The CCU 25 converts the supplied signal into a video signal and thereafter supplies the resultant signal to the video signal processing circuit 33. Thus, for example, an image as shown in FIG. 6 may be displayed on LCD 14.

According to a first embodiment, the endoscope 10 executes the stereo measurement of a subject as a measurement target based on optical data from the recording medium (such as the compact flash memory card), on which the optical data from the stereo optical adaptor 37 is recorded. This is performed by using an endoscope image in which a white subject is photographed as shown in FIG. 7.

According to the first embodiment, the endoscope 10 sets the measurement environment before actual stereo measurement and a standby mode for measurement needs to be prepared. Therefore, before describing the operation for actual measurement, the setting of the measurement environment will be described.

As disclosed in U.S. Pat. No. 6,063,023, the stereo measurement adaptor has varied optical characteristics that are used depending on the individual, even if the type of adaptor is the same. Therefore, optical data is measured in a producing step. The optical data includes the following information.

(A) Geometric-deformation correction formula of two optical systems
(B) Focusing distance of two lens systems
(C) Distance between optical axes of two lenses and position coordinates of the optical axes
(D) Positional information of attachment of the combination of the endoscope used for data measurement and the optical adaptor.

The above positional information (D) indicates position coordinates and an inclination angle of two areas in the field of view obtained from the endoscope image in which the white subject (such as a white sheet) is photographed by the combination of the data measurement endoscope and the optical adaptor as shown in FIG. 7.

The stereo measurement adaptor is attached to the endoscope insertion portion after capturing the optical data. In the endoscope apparatus 10, the following processing is performed and the measurement environment is set:

1) The recording medium to which the optical data of the stereo measurement adaptor is recorded is attached and the data is read.
2) The optical adaptor is attached to the endoscope insertion portion 11 which is actually used, the white subject is photographed as shown in FIG. 7, and the positional information of the attachment is obtained. The obtained positional information indicates the same contents as that of the positional information included in the optical data.
3) The positional information in the optical data is compared with the positional information obtained in 2). The information in (A) and (C) is corrected to data suitable to the endoscope which is actually used, among the optical data recorded on the recording medium. Specifically, the rotation correction for coordinate is performed.
4) In some cases, characteristics of the CCU or video capturing circuit used for the data measurement in the producing step are different from characteristics of the endoscope used for actual measurement, and the zoom ratio of the image is varied depending on the type of apparatus. In these cases, the difference of the characteristics is previously examined and the optical data recorded on the recording medium is corrected so as to match the zoom ratio.
5) The optical data obtained by the above process after correction is set by calibration data used to set the measurement environment.
6) A transform table for geometric deformation correction in the present endoscope apparatus is formed by using the calibration data.
7) An inverse transform table for obtaining coordinates on the original image before correction to the coordinates on the corrected image is formed.
8) The calibration data shown in 5), the transform table obtained in 6), the inverse transform table obtained in 7), and information on the measurement environment indicating the type of apparatus are set as data on the measurement environment as a unit. The data on the measurement environment is recorded to, for example, the compact flash memory card 23 for storing the data in the apparatus.

The above processes relate to the setting of the measurement environment.

Next, a description is given of the rotation correction shown in 3) by using calculating formulae.

It is assumed that the geometric deformation correction formula before rotation correction has the following relations.

$$x' = fx(x, y), y' = fy(x, y) \quad (1)$$

Herein, (x', y') are coordinates after the geometric deformation correction, (x, y) are arbitrary coordinates on the image before the geometric deformation correction (coordinate on the original image), fx(x, y) is a function for transforming the coordinate (x, y) on the original image before the geometric deformation correction to the x coordinate after correction, and fy(x, y) is a function for transforming the coordinate (x, y) on the original image before the geometric deformation correction to the y coordinate after correction.

When the positional information in the optical data before correction is compared with the positional information on the actually used endoscope, it is assumed that reference symbol A denotes a rotation matrix indicating the difference between both positional information. Then, the geometric deformation correction formula after correction is performed as follows.

$$(x'', y'') = A \cdot (x', y') + (a, b) \quad (2)$$

Herein, (x'', y'') are coordinates after the geometric deformation correction, including the rotation correction (coordinate on the corrected image), (x', y') are coordinates after the geometric deformation correction, and (a, b) is the amount of positional shift in the x direction and in the y direction.

When the matrix is developed by substituting the formula (1) for the formula (2), the following relationships are obtained. The relationships are shown in FIG. 8.

$$x'' = fx'(x, y), y'' = fy'(x, y) \quad (3)$$

Herein, (x'', y'') are coordinates after the geometric deformation correction including the rotation correction (coordinate on the corrected image), (x, y) are arbitrary coordinates on the image before the geometric deformation correction and the rotation correction (coordinate on the original image), fx'(x, y) is a function for obtaining the x coordinate on the corrected image by performing the geometric deformation correction and the rotation correction of the coordinate (x, y) on the original image, and fy'(x, y) is a function for obtaining the y coordinate on the corrected image by performing the geometric deformation correction and the rotation correction of the coordinate (x, y) on the original image.

The position coordinate of the optical axis can be expressed by the above-mentioned relationships by using the rotation matrix A and the amount of positional shift (a, b).

When the transform table is formed, the inverse transform is simultaneously obtained in the above 7), When transforming the coordinate on the original image into the coordinate on the corrected image by using the formula (3), the coordinate (x, y) on the original image is stored at a portion corresponding to the coordinate (x'', y'') in the inverse transform table including the coordinates having a one-to-one corresponding relationship to the coordinates on the corrected image.

The coordinate transformed by the formula (3) is normally obtained as a real number. Therefore, the value needs to be an integer to match the inverse transform table.

Since the coordinate on the original image is transformed to the coordinate on the corrected image by the transform formula, the value on the original image is not included directly in the inverse transform table. In this case, by interpolating the above value with an adjacent point, the coordinates on the original image can appropriately be included at all positions in the inverse transform table.

When the inverse transform formula of the transform formula (1) is previously determined and when the inverse transform formula is obtained by the formula transform based on the transform formula (1), the inverse transform table may be obtained directly by using the inverse transform formula.

An inverse matrix of the rotation matrix used in the formula (2) is expressed by $A^{-1}$, and a formula for returning the coordinate on the corrected image to the coordinate before positional shift correction is as follows.

$$(x', y') = A^{-1} \cdot (x'', y'') \cdot (a, b) \quad (4)$$

Herein, (x', y') are coordinates before correcting the positional shift, in which only the geometric deformation is corrected, (x'', y'') are coordinates after correcting geometric deformation, including the rotation correction, coordinate on the corrected image and (a, b) is the amount of positional shift in the x direction and in the y direction.

Thus, if defining the inverse transform formula for correcting the geometric deformation upon measuring the optical characteristics as functions gx and gy, the following relational formulae are established.

$$x = gx(x', y'), y = gy(x', y') \quad (5)$$

Herein, (x, y) are coordinates before correcting the geometric deformation (coordinate on the original image), (x', y') are coordinates before correcting the positional shift, in which only the geometric deformation is corrected, gx(x', y') is an inverse transform function for obtaining the x coordinate before correction in the geometric deformation correction, and gy(x', y') is an inverse transform function for obtaining the y coordinate before correction in the geometric deformation correction.

By developing the matrix of the formula (4) and substituting it for the formula (5), a transform formula for transforming the coordinate on the corrected image into the original image is expressed as follows. This relationship is shown in FIG. 8.

$$x = gx'(x'', y''), y = gy'(x'', y'') \quad (6)$$

Herein, (x, y) are arbitrary coordinates (coordinates on the original image) on the image before the geometric deformation correction or the rotation correction, (x'', y'') are coordinates (coordinate on the corrected image) after the geometric deformation correction including the rotation correction, gx'(x, y) is a function for obtaining the x coordinate on the original image before the geometric deformation correction and the rotation correction of the coordinate (x'', y'') on the corrected image, and gy'(x, y) is a function for obtaining the y coordinate on the original image before the geometric deformation correction and the rotation correction of the coordinate (x'', y'') on the corrected image.

The information on the measurement environment shown by the above 8) is information indicating the type of data on the measurement environment (that is, the calibration data and the transform table). Therefore, the following information is included.

(a) The type of stereo measurement adaptor and the individual identification number (b) The type of the endoscope insertion portion and the individual identification number (c) TV type such as NTSC (d) The type of CCU (e) The type of video capturing circuit Since the CCU and the video capturing circuit may be provided as modules of the endoscope, they may be replaced with the endoscope according to an exemplary embodiment of the present invention.

After setting the measurement environment as described above, the subject can be photographed and the actual measurement can be executed.

The stereo measurement of the endoscope 10 is performed by: first, processing for reading optical information from the recording medium (such as the compact flash memory card), on which the optical data from the stereo optical adaptor 37 is recorded; second, processing for obtaining the positional information between the image pick-up device 43 in the endoscope tip portion 39 and the stereo measurement adaptor 37; third, processing for obtaining a position error based on the above-mentioned positional information and position information between the main endoscope and the stereo optical adaptor 37 obtained upon manufacturing; fourth, processing for correcting the optical data based on the position error; fifth, processing for forming the transform table for correcting the geometric deformation included in the photographed image; sixth, processing for coordinate-transforming the photographed image for measurement to form the corrected image by using the transform table; seventh, processing for matching two left and right images at an arbitrary point based on the corrected image; eighth, processing for obtaining the three-dimensional coordinates from the two left and right coordinates obtained by matching, the position coordinates of the optical axes, and the focusing distances; and ninth, processing for obtaining the measurement values such as distance between two points and the area based on the three-dimensional coordinates at a plurality of arbitrary points.

The CPU 26 subjects the stereo optical adaptor 37 to, for example, the first to fifth processing once, and controls the operation so that the processing results are recorded to the compact flash memory card 23 as data on the measurement environment. Subsequently, the stereo measurement is executed. Then, the CPU 26 loads the date on the measurement environment recorded on the compact flash memory card 23 on the RAM, thereby executing the sixth to ninth processing steps. Since the image is recorded to the detachable memory card, a similar memory card to which the image may be recorded is loaded to the present apparatus by using the other apparatus. Advantageously, the image recorded by another apparatus can easily be viewed on another apparatus.

The brightness of the photographed white image shown in FIG. 7 upon the second processing is determined in accordance with the gain of the CCU 25 and a shutter speed. The gain of the CCU 25 and the shutter speed of the image pick-up device 43 are automatically controlled to match the best condition. However, when capturing the white image, the gain of the CCU 25 may be set low and the shutter speed of the image pick-up device 43 may be set high. This causes the image to be dark, and thus, the mask shape of the optical adaptor (in other words, the field of view) may not be clearly photographed. This adversely influences measurement accuracy.

Thus, according to the first embodiment, the gain of the CCU 25 and the shutter speed are fixed by the CPU 26. Accordingly, the clear mask shape can be captured without fail, and a decrease in measurement precision may be prevented.

The above-mentioned data on the measurement environment comprises the calibration data after position correction, the transform table, the inverse transform table, and the information on the measurement environment. The data on the measurement environment is recorded to the detachable compact flash memory card 23.

According to the first embodiment, the image is recorded to the PCMCIA memory card 22 by the CPU 26 so that the image is recorded to a memory card different from the compact flash memory card 23 for recording the data on the measurement environment. Upon recording the image, the information concerning the measurement environment is simultaneously recorded from the data on the measurement environment as a part of the image file, or as another file associated with the image file. Further, the calibration data is recorded as part of the image file or as another file associated with the image file.

Upon selecting the recorded image from the list and executing the stereo measurement, it is determined whether the data on the measurement environment is the same as that of the selected image among the data on the measurement environment which has already been registered.

If the same data is registered, the same data on the measurement environment is read, the setting of the endoscope is changed, and the sixth processing step is performed to enter the measurement state. If the same data is not registered, the data on the measurement environment is formed by using the calibration data added to the image and sixth processing step is performed to enter the measurement state. Conveniently, the formed data on the measurement environment is registered in the measurement environment facility. Alternatively, since non-registration advantageously prevents the optical adaptor from being erroneously selected on the selecting screen of the optical adaptor shown in FIG. 9, the registration or the non-registration is selected, depending on the structure of the endoscope.

As mentioned above, under the measurement environment corresponding to the software loaded in the endoscope, the measurement environment can automatically be set for any image. Therefore, the re-measurement can easily be performed.

Further, the information recorded to the image may include the calibration data, the information on the measurement environment, and the data on the measurement environment including the transform table, etc. In this case, the data on the measurement environment data included in the image upon selecting the image and executing the measurement may be directly read and the sixth processing step may be performed. Thus, the preparation of the measurement is completed. However, in this manner, the data on the measurement environment is recorded together with the image and the required data capacity is large. The information on the measurement environment and the calibration data is several tens of Kbytes. Thus, it is exceedingly efficient for the capacity of the image that only the information on the measurement environment and the calibration data are recorded to the image.

After preparing the measurement, for example, when measuring the length of a crack 44 in FIG. 6, a measurement point is designated by a broken line to trace the crack 44 on the left of the screen. The CPU 26 searches for a corresponding point on the right of the screen at every designation of a new measurement point, obtains three-dimensional coordinates at the measurement point based on coordinates of the measurement point and the corresponding point, calculates a distance between two adjacent points based on the three-dimensional coordinates, calculates the sum of the distances, and displays the entire length of the crack 44 on the LCD 14.

Next, a description is given of the structure of the normal optical adaptor used for the endoscope 10 according to the first embodiment with reference to FIGS. 10 to 12.

FIGS. 10 and 11 show a state in which a normal optical adaptor 42 is mounted on the endoscope tip portion 39. The normal optical adaptor 42 is fixed by being screwed to the male screw 54 of the endoscope tip portion 39 using the female screw 53 of the fixing ring 38.

A pair of an illumination lens 41 and an objective lens 40 are provided for the tip of the normal optical adaptor 42. The objective lens 40 forms an image on the image pick-up device 43 arranged in the endoscope tip portion 39. The obtained image pick-up signal is supplied to the CCU 25 via the electrically connected signal line 43a and the endoscope unit 24. The CCU 25 converts the resultant signal into a video signal and supplies the converted signal to the video signal processing circuit 33. As a consequence, for example, an image shown in FIG. 12 is displayed on the LCD 14.

According to the first embodiment, the endoscope 10 performs the measurement using the normal optical adaptor by utilizing a comparison measurement method. Namely, the comparison measurement is performed by using a conventional dimension as a base on the screen.

For example, when a diameter of a circle shown in FIG. 12 is well-known, a pointer is placed at both ends of the diameter of the circle and a length La 45 between the two points is inputted. A length Lb 46 to be determined is obtained by the CPU 26, which performs a ratio calculation based on the length La. In this case, information concerning distortion characteristics of the lens is used to perform distortion correction to obtain the dimension more accurately. The distortion characteristics of the lens are previously recorded on the ROM 27, and the CPU 26 implements the comparison measurement so that data corresponding to the selected normal optical adaptor 42 is loaded to the RAM 2.

A detailed description is given of the control operation by the CPU 26 in the endoscope 10 characterized by the first embodiment with reference to FIGS. 13, 14A, and 14B.

Now, it is assumed that the capabilities of the endoscope 10 shown in FIG. 1 is turned on and is used. After power on, the CPU 26 executes a main program (refer to FIG. 13) and enters a standby mode executing a loop containing determination processing in steps S100, S101, S102, S103, and S109. Functions in steps S100, S101, and S102 are executed and the CPU 26 shifts to processing of the functions. Then, a function in step S103 is executed and the CPU 26 shifts to step S104.

In determination processing in step S103, the CPU 26 determines whether the optical adaptor attached to the endoscope tip portion 39 is set and whether the optical adaptor is attached. If it is determined that the optical adaptor is not set, in step S108, the CPU 26 determines whether the processing ends. If it is determined that the processing ends, the processing is completed. If it is determined that the processing has not ended, the processing returns to step S100.

Alternatively, if it is determined in step S103 that the optical adaptor is attached to the endoscope tip portion 39 and the attached optical adaptor is set, the CPU 26 shifts to processing in step S104. That is, the CPU 26 enters a standby mode for inputting a function for setting the optical adaptor by shifting to the determination processing in step S104.

When any optical adaptor is attached to the endoscope tip portion 39, the CPU 26 calls the function for setting the optical adaptor and shifts the processing to step S104 whereupon a signal for displaying the selecting screen of the optical adaptor based on the function for setting the optical adaptor by the processing is generated and the generated signal is supplied to the video signal processing circuit 33 (refer to FIG. 2). Accordingly, the CPU 26 displays the selecting screen of the optical adaptor shown in FIG. 9 on the LCD 14. That is, the selecting screen of the optical adaptor is a display screen for selecting any of an AT60D/60D or AT60S/60S stereo optical adaptor, and an AT120D or AT60D normal optical adaptor. A user views the selecting screen and selects the currently used optical adaptor by vertically moving a cursor (not shown) displayed on the screen by vertically moving the lever switch 48.

Thereafter, in the determination in step S105, the CPU 26 determines whether or not the user's selected optical adaptor is the normal optical adaptor. If it is determined in step S105 that it is the normal optical adaptor, in the processing in step S106, the CPU 26 sets a comparison measurement flag to 1 (TRUE), and shifts the processing to step 3107. On the other hand, if it is determined in step S105 that it is not the normal optical adaptor, the CPU 26 shifts the processing to step S107.

In processing in step S107, the CPU 26 determines whether the user's selected optical adaptor is the stereo optical adaptor. If it is determined in step S107 that it is the stereo optical adaptor, in step S108, the CPU 26 sets a stereo measurement flag to 1 (TRUE). The CPU 26 sets the measurement endoscope apparatus 10 to a standby mode for use until the user presses the measurement executing switch 51 of the remote controller 13. If it is determined in step S107 that it is not the stereo measurement adaptor, similarly, the CPU 26 controls the operation so that the endoscope 10 is in the standby mode for the use.

Since the endoscope 10 is generally in a state in which the subject is being photographed (i.e., live video image display state), the user presses the measurement executing switch 51 of the remote controller 13 and then the CPU 26 controls the video signal processing circuit 33 so as to display the still image. A routine program for the still image as shown in FIGS. 14A and 14B is executed.

The endoscope can select the image from a list of a plurality of images recorded to the PCMCIA memory card 22 (not shown) by vertically moving the lever switch 48. Thereafter, by pressing the measurement executing switch 51 of the remote controller 13, the CPU 26 allows the routine program for the selected image as shown in FIGS. 14A and 14B to be executed.

After the CPU detects the press of the measurement executing switch, in determination processing in step S111 in FIG. 14A, the CPU 26 determines whether or not the image is an image recorded to the PCMCIA memory card 22. If the image is the recorded one, the CPU 26 determines in determination processing in step S112 whether or not the image is a stereo measurement image.

If the image is the stereo measurement image, in determination processing in step S113, the CPU 26 determines whether or not the information on the measurement environment is added to the header of the image file. If the information is recorded, in determination processing in step S114, the CPU 26 determines whether or not the same information on the measurement environment exists in the data on the measurement environment recorded to the compact flash memory card 23. If YES, the data on the measurement environment is read and it is controlled so that the stereo measurement processing is performed in processing in step S115. After the stereo measurement ends, the measurement result is displayed or the apparatus 10 is set to enter a standby mode for purpose of the re-measurement.

If the same data on the measurement environment does not exist in the determination processing in step S114, in determination processing in step S117, the CPU 26 determines whether or not the calibration data is added to the header of the image file. If the calibration data is added to the image in the determination processing in step S117, in determination processing in step S118, the CPU 26 determines whether or not the calibration data added to the image corresponds to the software for the present measurement loaded to the present apparatus 10. If YES in step S118, in the processing in step S119, the calibration data is used, the data on the measurement environment is formed, and then it is controlled so that the stereo measurement processing is performed.

When the calibration data is not added to the image in the determination processing in step S117, when the calibration data added to the image does not correspond to the present software in the determination processing in step S118, or when the information on the measurement environment is not added to the header of the image file in the determination processing in step S113, a fact that the stereo measurement is impossible is displayed and the apparatus 10 is set to enter the standby mode so as to select another image.

If the image selected in the determination processing in step S112 is not the stereo measurement image, in determination processing in step S122, it is determined whether or not the image is for comparison measurement. If it is determined that the image is for comparison measurement, the information for correcting the deformation of the optical adaptor added to the image is read and the comparison measurement is executed. If the image is not for comparison measurement in the determination processing in step S122, a fact that neither the stereo measurement nor the comparison measurement can be performed is displayed and the apparatus 10 is set to enter the standby mode so as to select another image.

Further, when the image for measurement is an image which is a still image of a live video display image in the determination processing in step S111, if the stereo measurement flag is 1 (TRUE) in determination processing in step S126 in FIG. 14B, the data on the measurement environment of the stereo measurement adaptor selected on the screen shown in step S104 in FIG. 13 is read and the stereo measurement is performed.

When the stereo measurement flag is not 1 (TRUE) in the determination processing in step S126 and when the comparison measurement flag is 1 in determination processing in step S128, similarly to the above description, the distortion information of the normal optical adaptor selected by the screen shown in step S104 in FIG. 13 is read and the comparison measurement is executed.

When the comparison measurement flag is not 1 (TRUE) in the determination processing in step S128, the processing routine returns to step S103 in FIG. 13 and it is controlled so that the setting necessary for executing the measurement is confirmed again.

According to the first embodiment, not only the appropriate measurement program can be executed solely by the pressing the measurement executing switch 51 of the remote controller in the live video display, but also the information necessary for correct measurement is read and the appropriate program can be executed in the case of re-measurement using the image which has already been recorded solely by selecting the image and pressing the measurement executing switch 51 of the remote controller. That is, in the case of the re-measurement using the recorded image, the measurement is not performed by using mismatched data on the measurement environment and distorted information. Thus, incorrect measurements can be prevented.

Figure 15A:
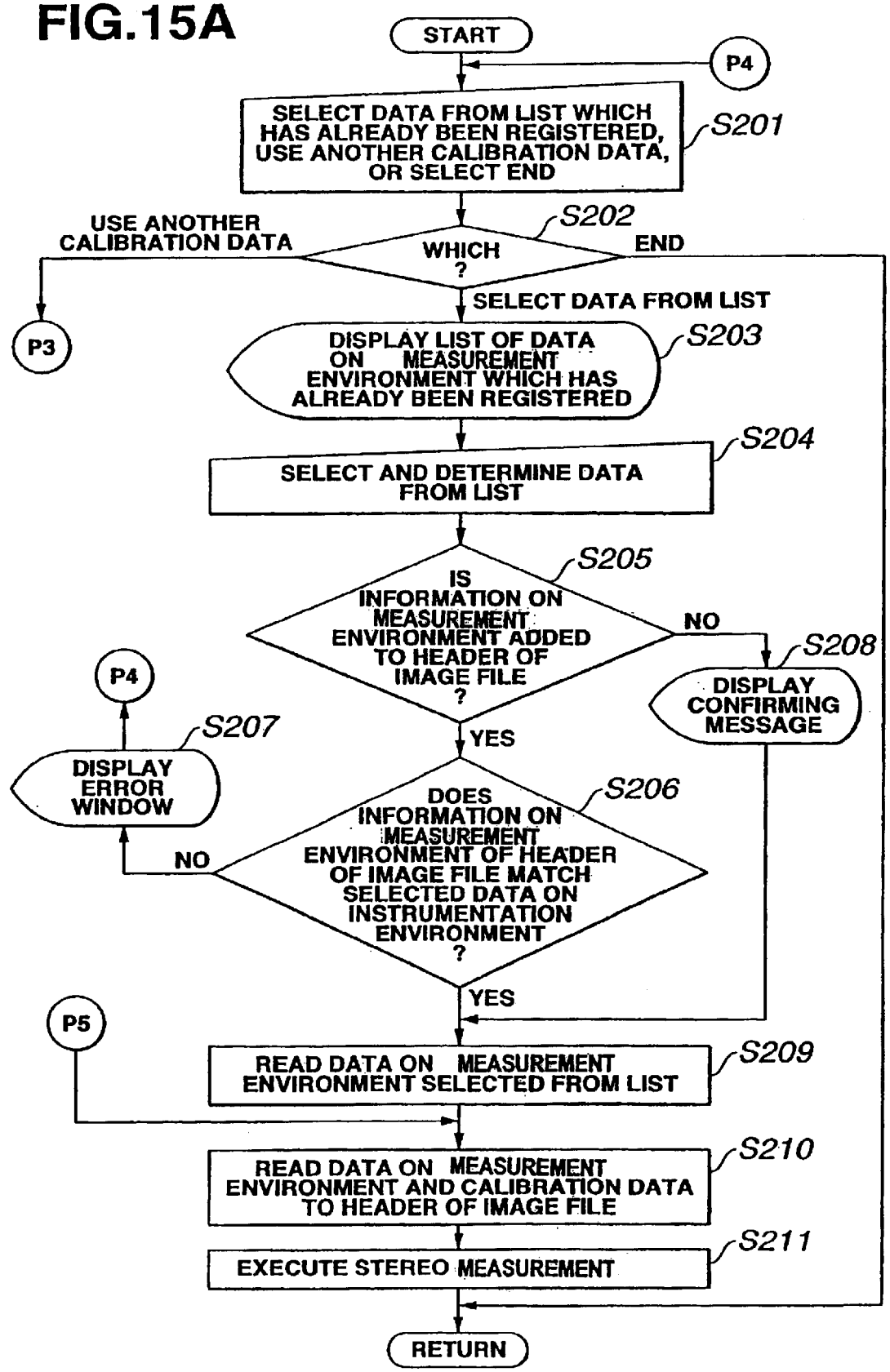
FIG. 15A is one part of a flowchart showing an example of control operation by a CPU, as a feature, according to a second embodiment of the present invention.
Figure 15B:
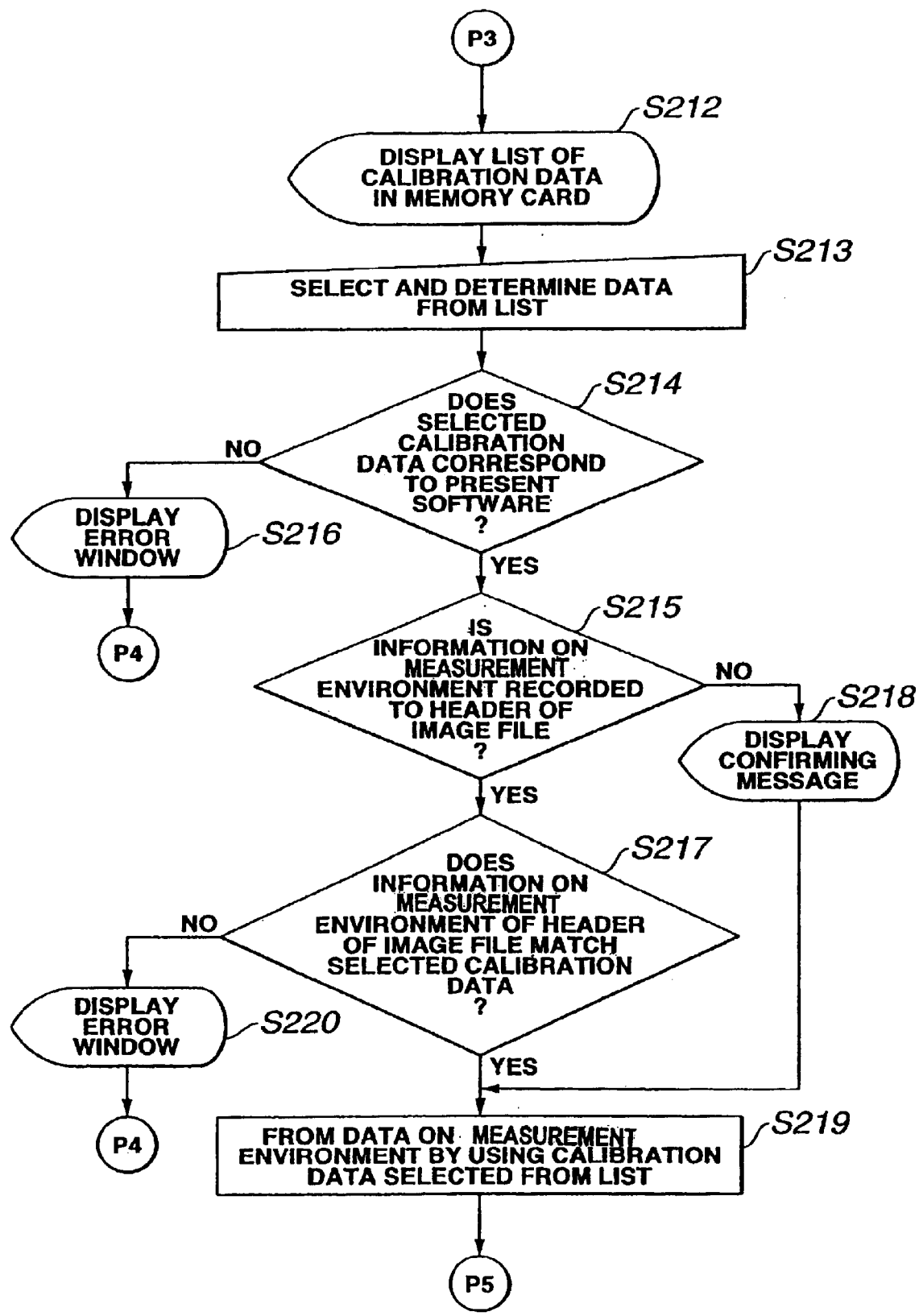
FIG. 15B is another part of the flowchart showing the example of the control operation by the CPU, as a feature, according to the second embodiment of the present invention.

Next, a description is given of a endoscope according to a second embodiment of the present invention with reference to FIGS. 15A and 15B.

FIGS. 15A and 15B are flowcharts showing examples of the control operation by a CPU in the endoscope, as a feature, according to the second embodiment.

The structure according to the second embodiment is substantially the same as that according to the first embodiment. Therefore, only different points are described, the same components are designated by the same reference numerals, and a description thereof is omitted.

According to the second embodiment, when neither the information on the measurement environment nor the calibration data is recorded to the image recorded to the recording medium, the program executed according to the first embodiment is improved and an additional function is provided for the program so as to promptly execute the appropriate measurement.

Specifically, the recorded stereo measurement image is selected and the measurement executing switch is pressed. Then, when the information on the measurement environment is not recorded to the header of the image file or a file different from the image file and when the information on the measurement environment is recorded to the header of the image file or the file different from the image file but the calibration data is not recorded, the user selects the appropriate data on the measurement environment which has already been recorded to the compact flash memory card. Then, the data on the measurement environment is read and it is controlled so that the stereo measurement is executed.

Further, when the user determines that the appropriate data on the measurement environment which has already been registered does not exist, the user selects the appropriate calibration data which is recorded to another image in the PCMCIA memory card. Then, the data on the measurement environment is formed by using the calibration data and the stereo measurement is executed.

In the operation for selecting the calibration data, if the functions of the stereo measurement include a function for copying only the calibration data and the information on the measurement environment as a part of the data on the measurement environment which has already been registered, to a memory card different from the recording medium for recording the image and the data on the measurement environment, the memory card is attached to the present apparatus 10 and the appropriate data may be selected from a plurality of pieces of the calibration data recorded to the memory card.

The present function can easily be applied not only to the stereo measurement but also the comparison measurement.

According to the second embodiment, when NG is obtained in step S113 or in step S117 in FIG. 14A according to the first embodiment, the processing shown in FIGS. 15A and 15B is operated. That is, when the information on the measurement environment is not added to the header to the image file in the determination processing in step S113 or when the calibration data is not added to the header of the image file in the determination processing in step S117, the processing routine advances to step S201 in FIG. 15A.

In step S201, the user determines whether the measurement is performed by using the data on the measurement environment which has already been registered, the measurement is performed by using the calibration data and setting the measurement environment, or this processing ends and the measurement is performed by using another image. Then, processing is performed which corresponds to the determination.

When data is selected from the data on the measurement environment in step S201, as shown in step S203, the list of the data on the measurement environment which has already been registered is displayed and the user selects the appropriate data.

In determination processing in step S205, it is determined whether or not the information on the measurement environment is added to the image. If the information on the measurement environment is added in step S205, in determination processing in step S206, the contents of the information on the measurement environment added to the image matches the contents of the selected data on the measurement environment in the comparison. If matching, the processing routine advances to step S209. If not matching, an error message is displayed as shown in step S207 and the apparatus enters the standby mode in which the correct data on the measurement environment or the correct calibration data is selected again in step S201.

If the information on the measurement environment is not added to the image in the determination processing in step S205, the contents of the selected data are displayed and the user confirms the data again. After that, the processing routine advances to step S209.

After reading the selected data on the measurement environment in step S209, the stereo measurement is executed.

On the other hand, when another calibration data is selected in step S201, the processing routine passes through the determination processing in step S202 and advances to step S212 in FIG. 15B. After attaching the memory card to which the appropriate calibration data is recorded to the apparatus 10, the list of the calibration data is displayed as shown in step S212. After the user selects the appropriate calibration data, in determination processing in step S214, it is determined whether or not the selected calibration data corresponds to the present software. If YES in step S214, the processing routine advances to step S215. If NO in step S214, the error message is displayed as shown in step S216 and the processing routine returns to step S201 in FIG. 15A whereupon the apparatus enters the standby mode so that the correct data on the measurement environment or the correct calibration data is selected again.

In determination processing in step S215, it is determined whether or not the information on the measurement environment is added to the image. If the information on the measurement environment is added to the image, in step S217, the contents are compared with the contents of the selected calibration data. If both contents match each other, the processing routine advances to step S219. If they do not match, as shown in step S220, the error message is displayed and, in step S201 in FIG. 15A, the apparatus enters the standby mode so that the correct data on the measurement environment or the correct calibration data is selected in step S201 in FIG. 15A.

When the information on the measurement environment is not added to the image in step S215, the contents of the selected data are displayed and the user confirms the contents again. Then, the processing routine advances to step S219.

The data on the measurement environment is formed from the selected calibration data selected in step S219. After that, the stereo measurement is executed.

Step S209 or step S219 is completed and, then, the information on the measurement environment and the calibration data may be recorded to the header of the image file in accordance with the user's desire before executing the stereo measurement.

The capacity of the calibration data is several tens Kbytes and the information on the measurement environment is several Kbytes in many cases. Therefore, only the information on the measurement environment is to be recorded to the image for purpose of reduction of one image file in some cases.

When the information on the measurement environment and calibration data are recorded to a file different from the image file, it is considered that the file of the information on the measurement environment and of the calibration data which are recorded in association with the image might be lost or reduced for some reason.

Conventionally, the re-measurement cannot be performed with the above-mentioned image. Alternatively, the working for setting the measurement environment until the actual re-measurement is complicated.

On the contrary, according to the second embodiment, solely by selecting the data on the measurement environment and the calibration data from the list of the data on the measurement environment which has already been registered and the list of the calibration data which is recorded to another memory card, the measurement environment can easily be set and the re-measurement can promptly be performed.

Further, it is confirmed whether or not the data selected from the list matches the image. Thus, advantageously, the number of cases in which the measurement is performed in the mismatched state is reduced.

Figure 16A:
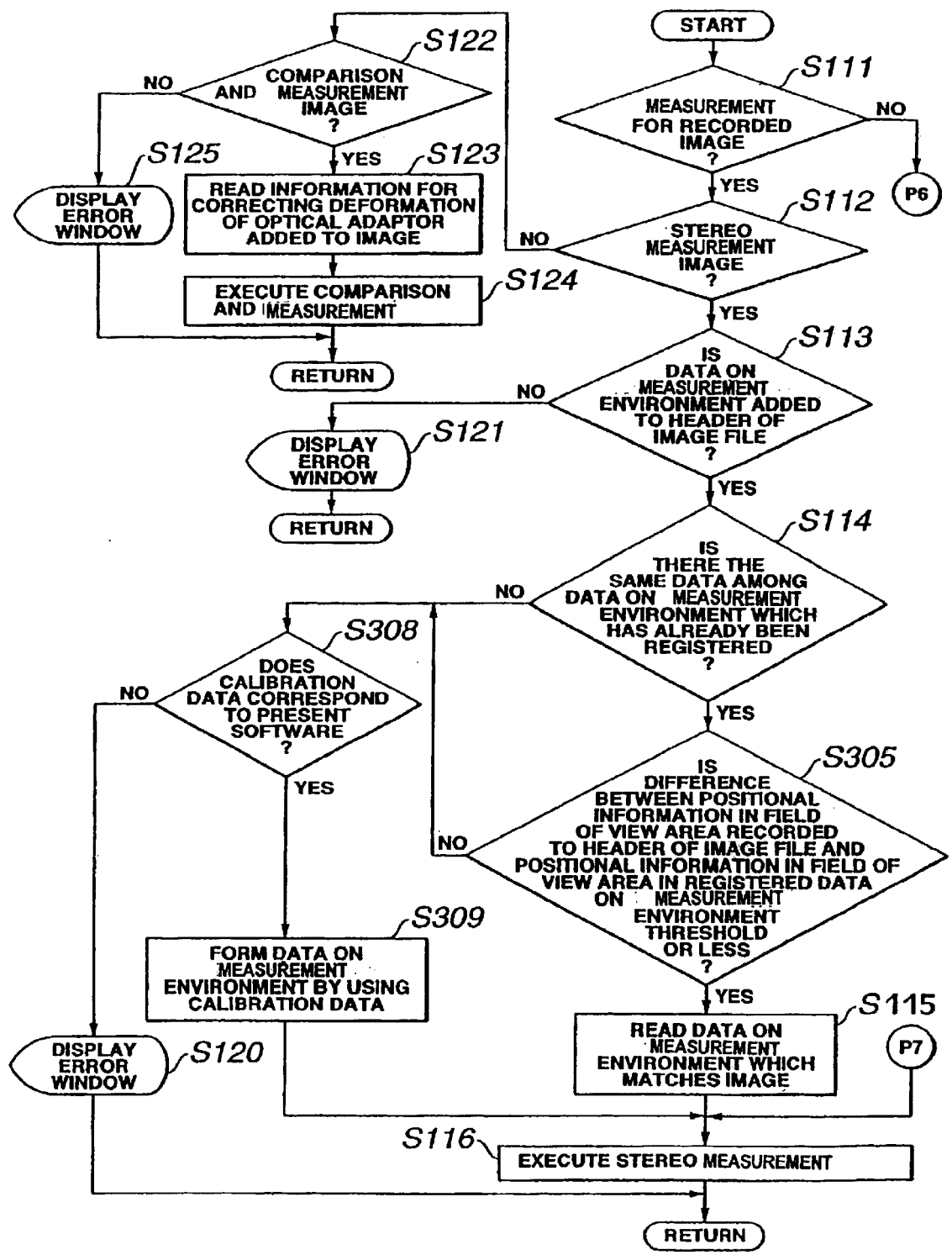
FIG. 16A is one part of a flowchart showing an example of control operation by a CPU, as a feature, according to a third embodiment of the present invention.
Figure 16B:
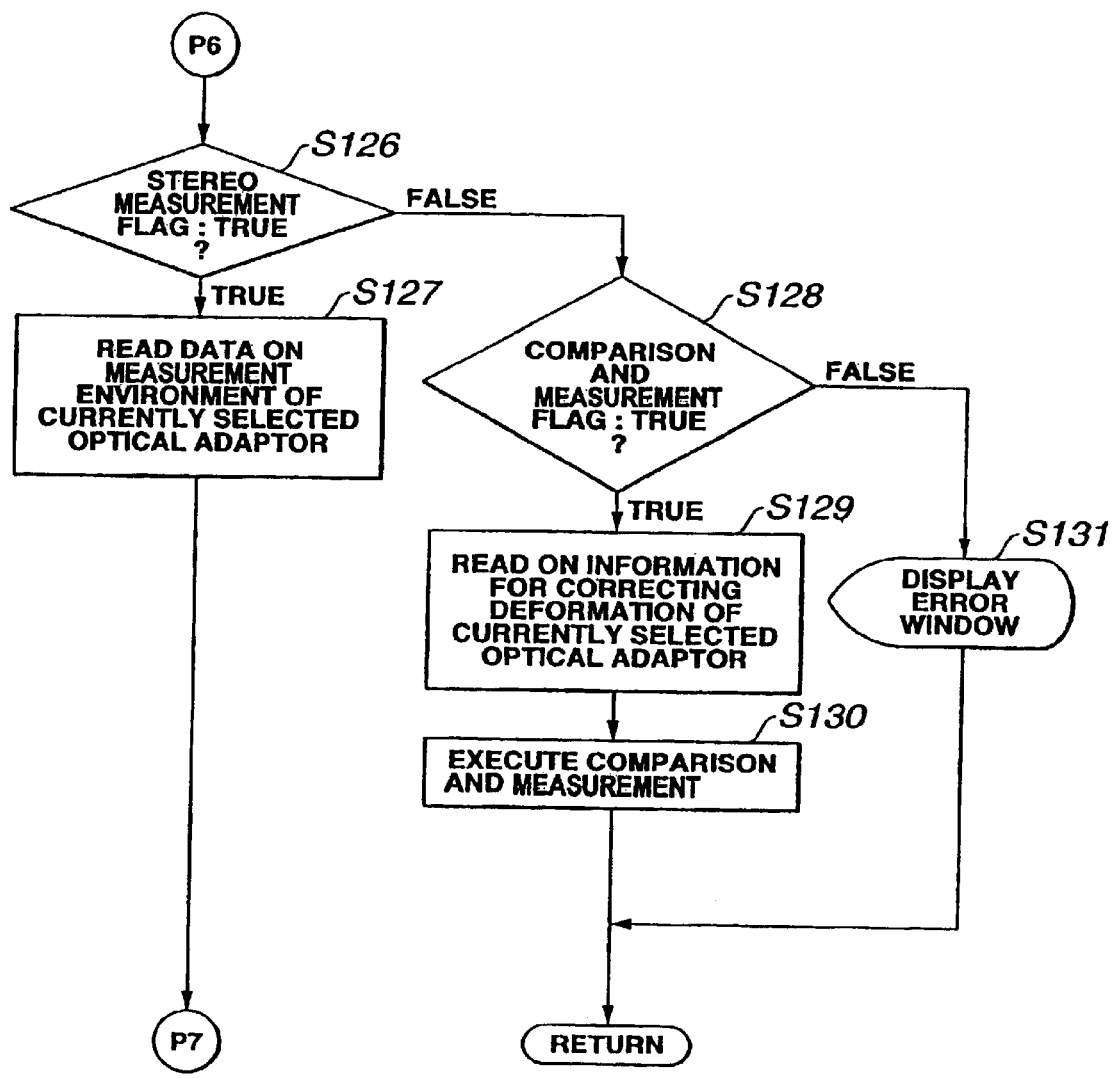
FIG. 16B is another part of the flowchart showing the example of the control operation by the CPU, as a feature, according to the third embodiment of the present invention.

Next, a description is given of a endoscope according to a third embodiment of the present invention with reference to FIGS. 16A and 16B.

FIGS. 16A and 16B are flowcharts showing the control operation by a CPU in a endoscope as a feature according to the third embodiment.

The third embodiment is substantially the same as the first embodiment. Therefore, only different points are described and the same reference numerals denote the same components. A description of the same components is omitted.

According to the third embodiment, the contents of the information positional relationship of the attachment of the optical adaptor included in the calibration data added to the image are compared with the contents of the information on the positional information included in the data on the measurement environment which has already been registered. Then, when the difference is larger than a predetermined threshold, processing for measurement using the calibration data added to the image is added to the functions according to the first embodiment, including the functions shown in the second embodiment.

In the endoscope 10, the stereo measurement image for measurement is selected from the list of a plurality of images recorded to the PCMCIA memory card 22 (not shown). The measurement executing switch 51 of the remote controller 13 is pressed and the CPU 26 executes the routine program shown in FIGS. 16A and 16B for the selected image.

Steps S111 to S114 in FIG. 16A are the same as those according to the first embodiment.

In determination processing in step S114, it is determined whether or not there is the same information on the measurement environment added to the image among the data on the measurement environment recorded to the compact flash memory card 23. If YES in step S114, in determination processing in step S305, it is determined whether or not the difference between the positional information in the area of the field of view included in the calibration data added to the image and the positional information in the area of the field of view included in the registered data on the measurement environment is smaller than a predetermined threshold.

If the difference is smaller than the threshold in step S305, it is controlled so that the data on the measurement environment which matches the image is read and the stereo measurement processing is performed. After completing the stereo measurement, the measurement result is displayed or the endoscope 10 enters the standby mode for re-measurement.

If the difference is not smaller than the threshold in step S305, in determination processing in step S308, it is determined whether or not the calibration data added to the image corresponds to the software for the present measurement loaded to the present measurement endoscope apparatus 10. If YES in step S308, in processing in step S309, it is controlled so that the data on the measurement environment is formed by using the calibration data and the stereo measurement processing is performed.

On the other hand, if the calibration data added to the image does not correspond to the present software in the determination processing in step S308, a fact that the stereo measurement is impossible is displayed and the endoscope 10 enters the standby mode so as to select another.

Accordingly, the photographing state of the white image to be photographed to examine the position in the area of the field of view is changed due to some reason even when the information on the measurement environment indicating the type of the device used upon photographing image matches. In association therewith, the number of cases in which the measurement precision is suppressed due to the change in the information on the positional relationship. Further, the image measurement can be performed by using the calibration data which has already been added to the image and by automatically setting the measurement environment. Thus, the measurement can be prepared easily and promptly with high safety.

The setting of the measurement environment for stereo measurement is completed and the corrected image of the still image or the stereo measurement image recorded to the recording medium is formed by using the data on the measurement environment. Then, the screen for stereo measurement is displayed as shown in FIG. 17 and the apparatus enters the standby mode so that the user designates the measurement point.

Figure 17:
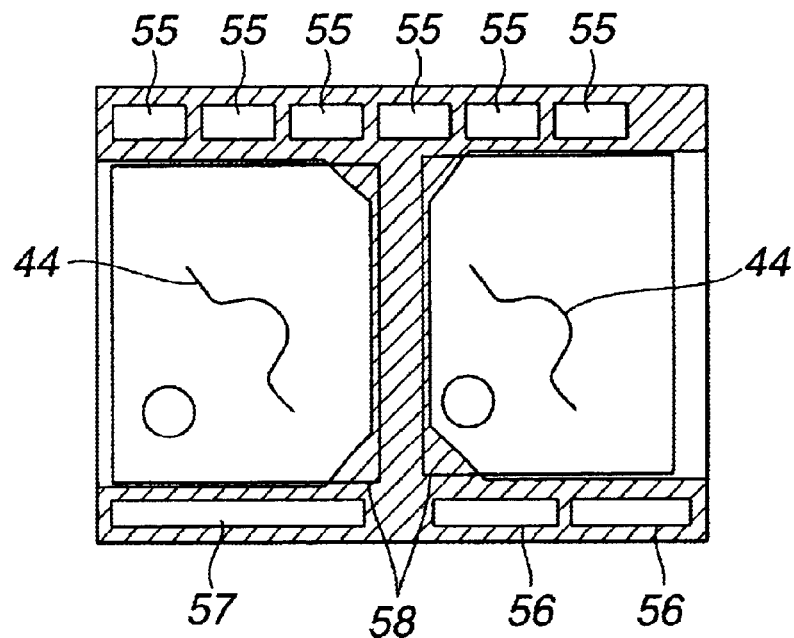
FIG. 17 is a diagram showing an example of a measurement screen on which a frame of a measurement field of view area is overlapped and displayed on a subject image.
Figure 18:
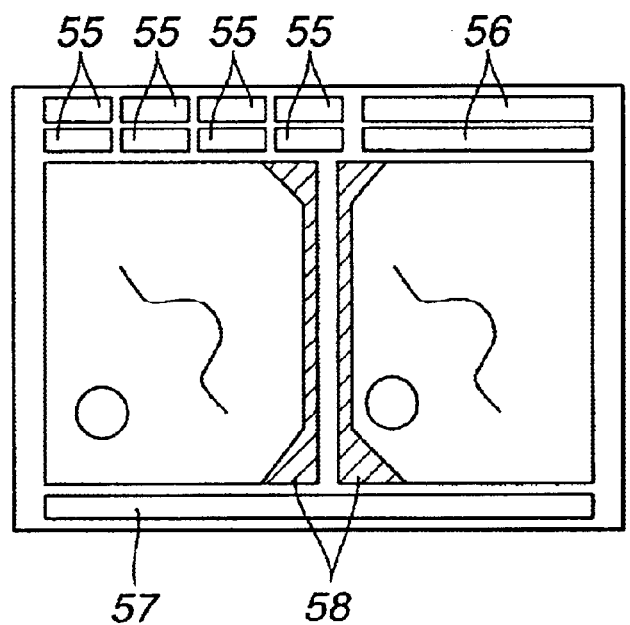
FIG. 18 is a diagram showing an example of a measurement screen on which left and right fields of view areas are cut out and displayed.

FIG. 17 shows an example in which various menu buttons 55 for executing the measurement functions, a message display column 57 for displaying the message of the operation, and various-value display columns 56 for displaying the measurement result (numerical value) are displayed on the original image, excluding the two areas of right and left fields of view.

Since the measurement size and the position in the two areas of the field of view are predetermined by the setting value of the optical adaptor, the size and position which are actually measured can be determined by correcting the optical data formed upon manufacturing in accordance with the attachment to the actually used endoscope.

In stereo measurement, the subject cannot be measured when the subject is not photographed on the left and right areas in the field of view. Therefore, it is necessary to measure the subject by designating the point in the measurement area in the field of view.

Thus, in the present disclosure, advantageously, the user can easily recognize the point within the measurement range by the following functions, and it is possible to prevent the measurement miss due to the designation of the point out of the measurement range.

That is, one of the functions is to display a frame of a measurement area in the field of view 58 which is determined as mentioned above, on the measurement image as shown in FIG. 17.

Another function is to change the shape of a cursor depending on whether the cursor position is within the area in the field of view 58 or out of the area 58. Because the point is designated within the measurement area (not shown) by horizontally or vertically moving the cursor on the screen by the lever switch of the remote controller. For example, the shape of the cursor is like cross within the area in the field of view 58 or it is like an arrow out of the area in the field of view 58.

Further, another function is to control the operation only within the area in the field of view 58 to designate the point.

Furthermore, another function is to display an alarm message when the point is designated out of the area in the field of view 58.

In addition, another function is to cut off the measurement area in the field of view 58 from the image, and to paste and display it on the screen dedicated for the measurement.

The size and position of the measurement area in the field of view 58 can be obtained by setting the measurement environment. Therefore, when the live video image is displayed after selecting the stereo measurement adaptor upon setting the optical adaptor in FIG. 9, the control operation is performed so that the frame is displayed. Then, the size and the position of the measurement area in the field of view 58 can become indexes for confirming whether or not the subject is correctly photographed on the left and right sides upon photographing the stereo measurement image.

According to the first to third embodiments of the present invention, when the image which has already been recorded is subjected to the re-measurement, the measurement using the image which does not correspond to the image for measurement is prevented, and the measurement can be executed corresponding to the correct optical adaptor by easy operation without the user's consideration of the type of the optical adaptor, irrespective of the current setting status of the apparatus. The operability is improved upon re-measurement and the examining efficiency is also improved.

Since a large capacity of the recording medium is not necessary to obtain the above-mentioned advantages, the apparatus can be realized by using an inexpensive recording medium.

Further, since the re-measurement is not necessary on the apparatus on which the image is actually photographed, the re-measurement can be performed on another apparatus with easy operation by attaching the recording medium, to which the image is recorded, to the other apparatus.

Thus, the convenience is exceedingly improved and an endoscope which executes measurements with high performance can be provided as a relatively inexpensive system.

That is, in the present invention, the endoscope comprises means for recording the information on the measurement environment and the calibration data together with the measurement image, means for selecting the measurement image which has already been recorded and executing the measurement processing, and means for automatically setting the measurement environment using the calibration data recorded to the measurement image. Accordingly, solely by selecting the measurement image which has already been recorded and pressing the measurement executing switch, the measurement environment is automatically set based on the information on the measurement environment and the calibration data which are added to the measurement image and the measurement processing can promptly be executed.

Further, the endoscope comprises means for searching the same information on the measurement environment which is recorded to the measurement image from the data which has already been managed in the apparatus by referring to the information on the measurement environment, and means for automatically changing the setting of the measurement environment by using the data as the search result. Thus, when the measurement image which has already been recorded is selected and the measurement executing switch is pressed, if there is the data on the measurement environment which is the same measurement information as the selected measurement image in the apparatus, the measurement processing can be executed by using the data on the measurement environment which has already existed without forming the data on the measurement environment again. The time for preparing the measurement is substantially reduced.

Furthermore, the endoscope comprises means for copying the measurement image recorded in the apparatus together with the information on the measurement environment and the calibration data to the detachable recording medium, and means for capturing the image copied to the recording medium to the apparatus together with the information on the measurement environment and the calibration data. Thus, not only the image for measurement can be subjected to the re-measurement on another endoscope, but also the same advantages as those described above can be obtained.

Alternatively, the above-mentioned measurement processing can be performed based on the data on the measurement image obtained by the endoscope on the single measurement apparatus as another apparatus or on the single PC.

If the calibration data is not recorded to the recording medium together with the measurement image for reason of a medium capacity for recording the image, in the case of selecting the image and performing the re-measurement, it can be searched whether or not the same data on the measurement environment exists in the apparatus by referring to the information on the measurement environment which is recorded together with the image. If the same data of the measurement environment exists in the apparatus, the data is used and the re-measurement can promptly be performed.

Moreover, if the information on the measurement environment and the calibration data are not recorded to the measurement image for some reason, means for informing it is provided. Therefore, a person performing the measurement can perform the measurement without considering whether or not the measurement environment of the selected image is recorded. In this case, the data on the measurement environment which has already existed in the apparatus is displayed and the appropriate data on the measurement environment is selected, thereby performing the measurement.

Next, a description is given of a endoscope and measurement software according to a fourth embodiment of the present invention with reference to FIGS. 1 to 12, and FIGS. 19 to 23A and 23B.

Figure 19:
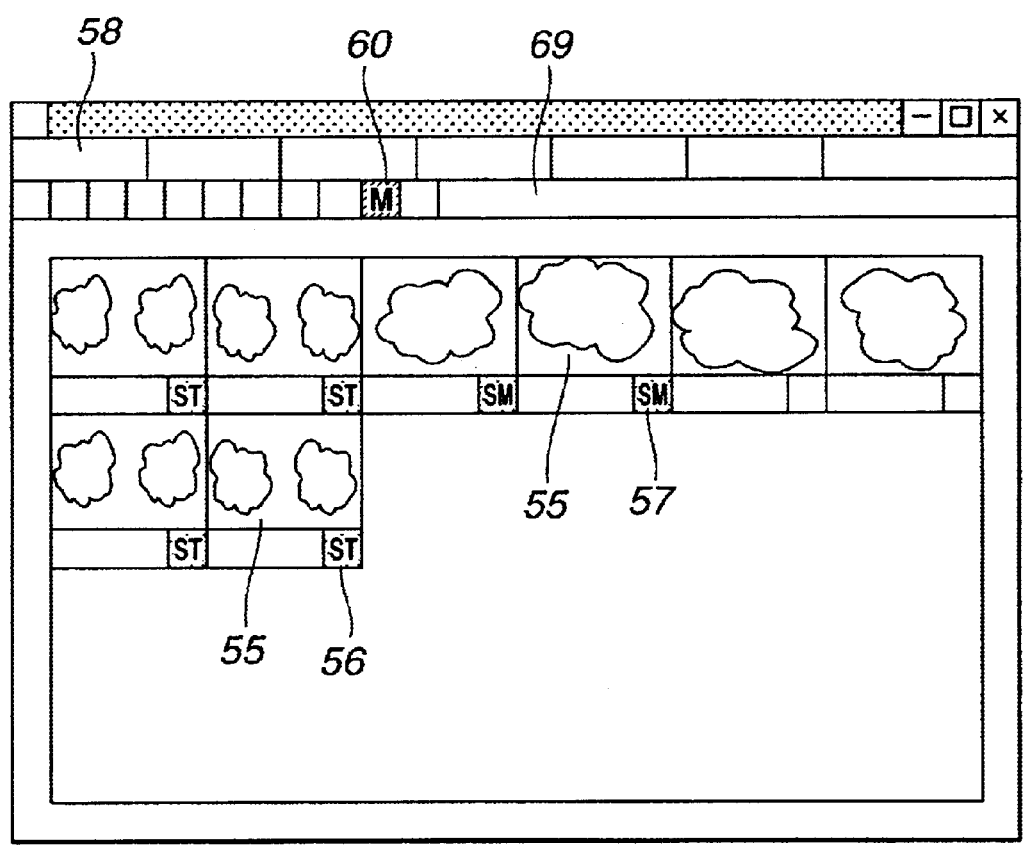
FIG. 19 is a diagram showing a display example of a thumbnail screen according to a fourth embodiment of the present invention.
Figure 20:
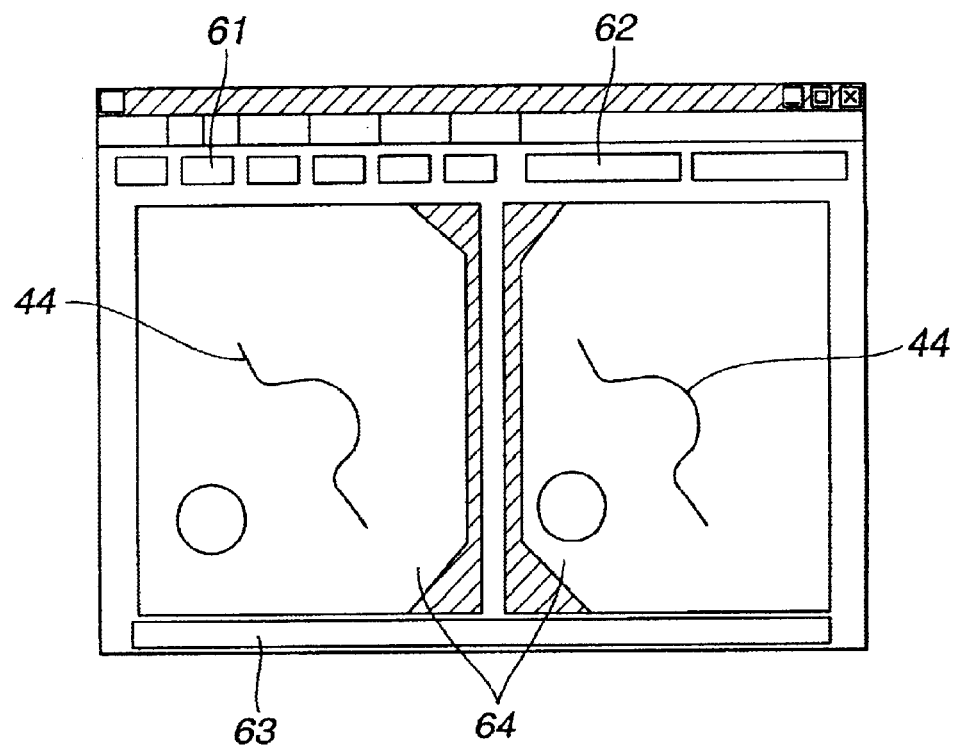
FIG. 20 is a diagram showing a display example of a screen of a stereo optical adaptor according to the fourth embodiment.
Figure 21:
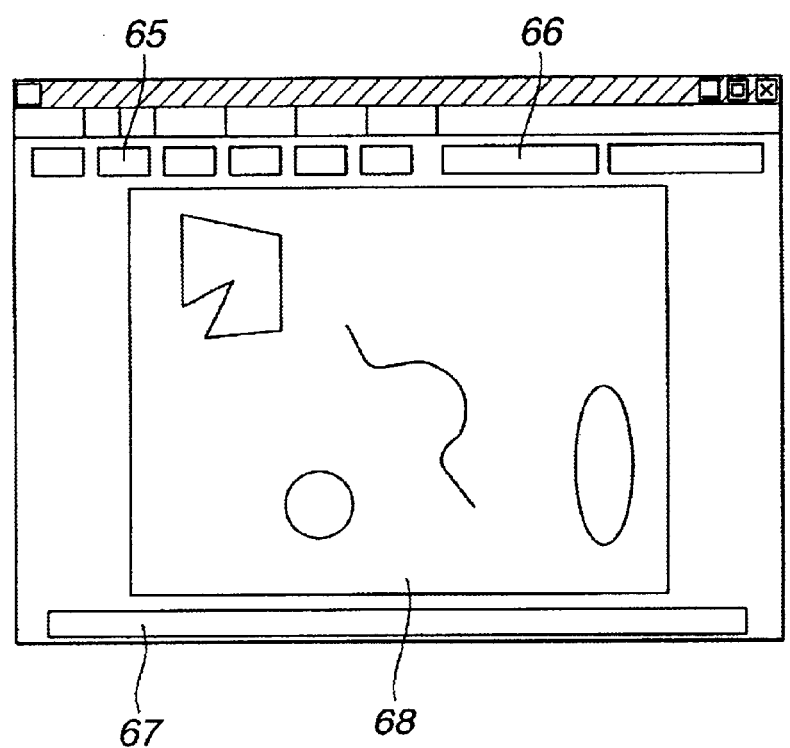
FIG. 21 is a diagram showing a display example of the screen of a normal optical adaptor according to the fourth embodiment.
Figure 22A:
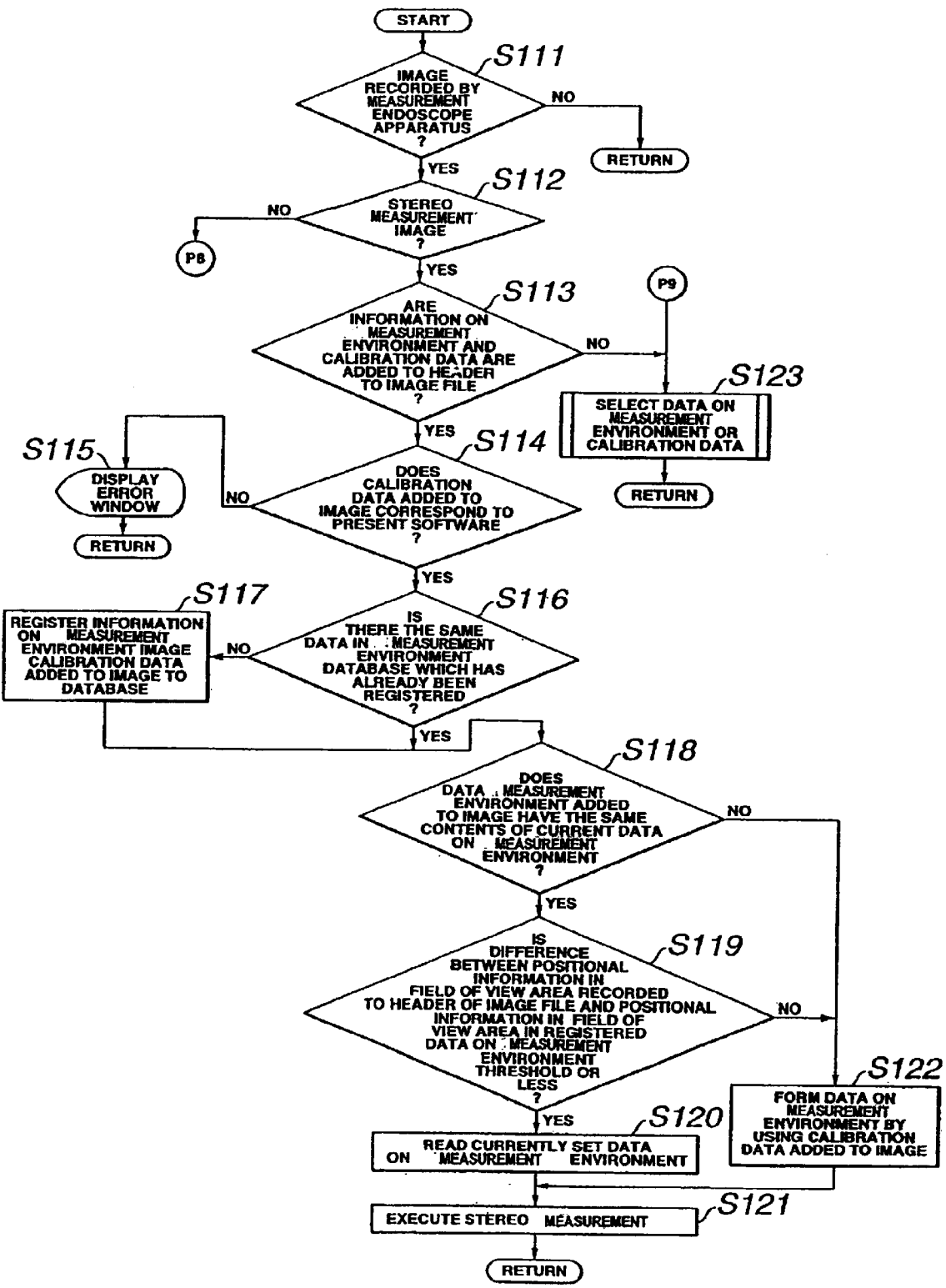
FIG. 22A is one part of a first flowchart showing an example of control operation of measurement software as a feature according to the fourth embodiment.
Figure 22B:
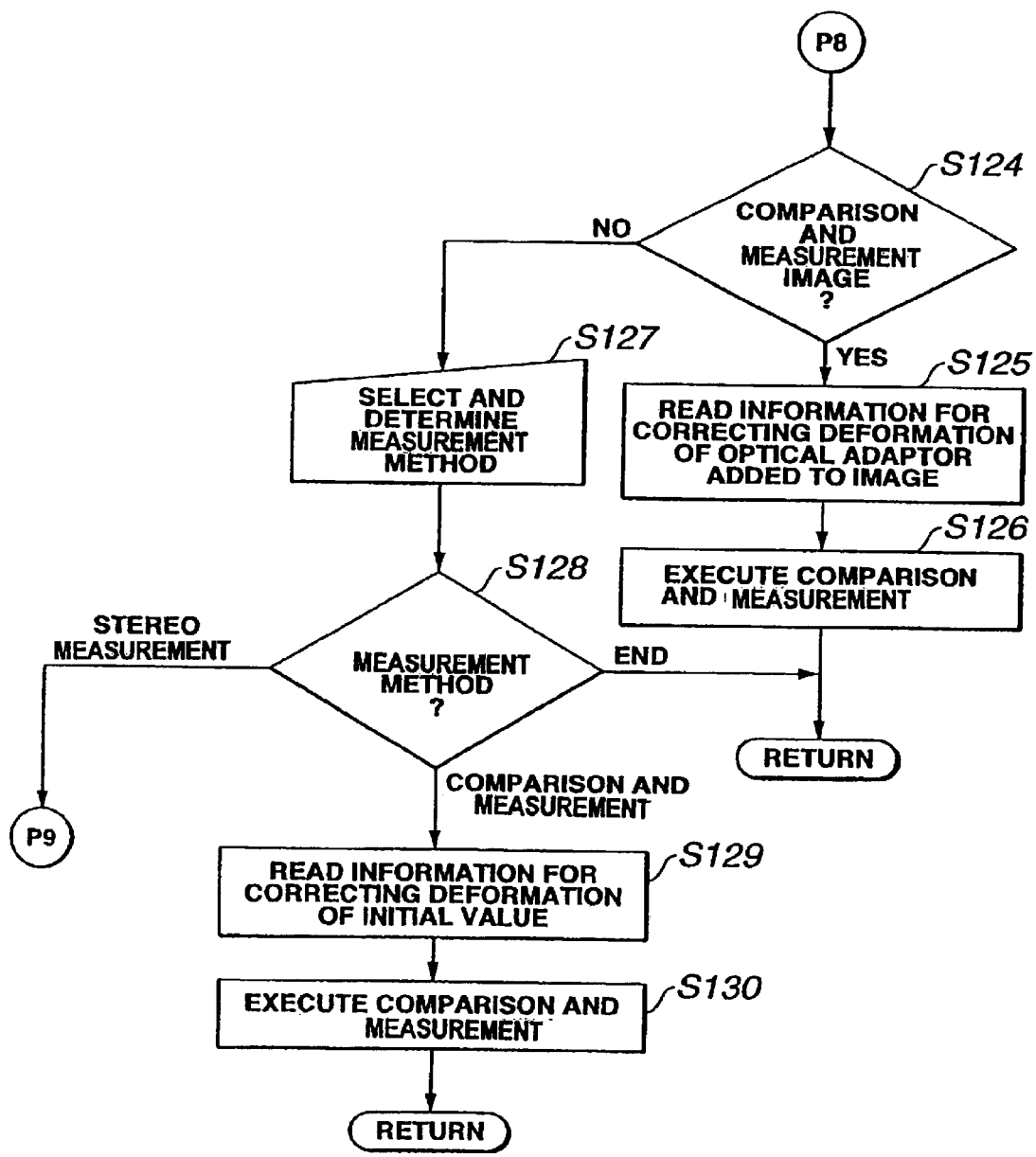
FIG. 22B is another part of the first flowchart showing the example of the control operation of the software as the feature according to the fourth embodiment.
Figure 23A:
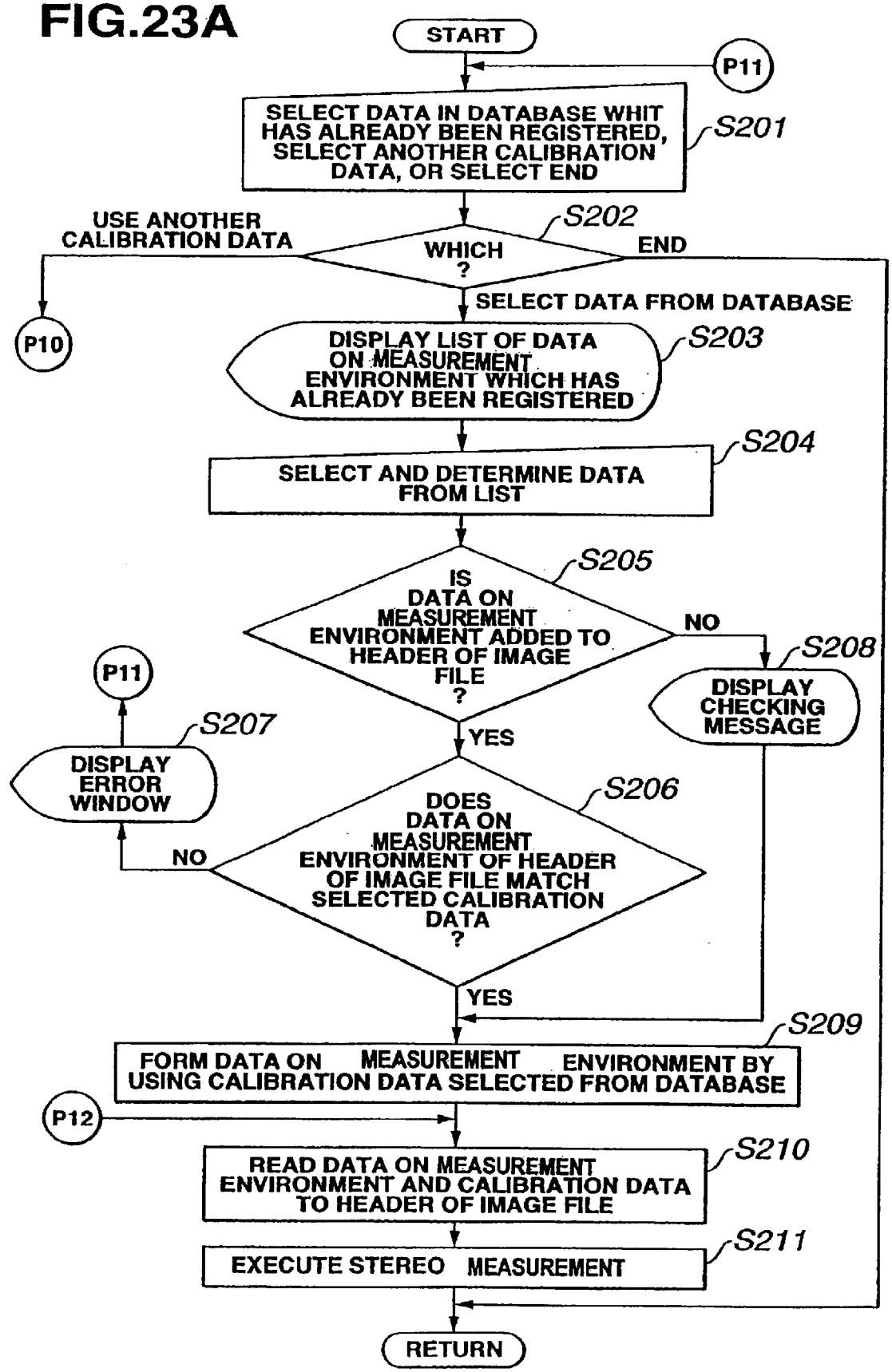
FIG. 23A is one part of a second flowchart showing an example of control operation of software as a feature according to the fourth embodiment.
Figure 23B:
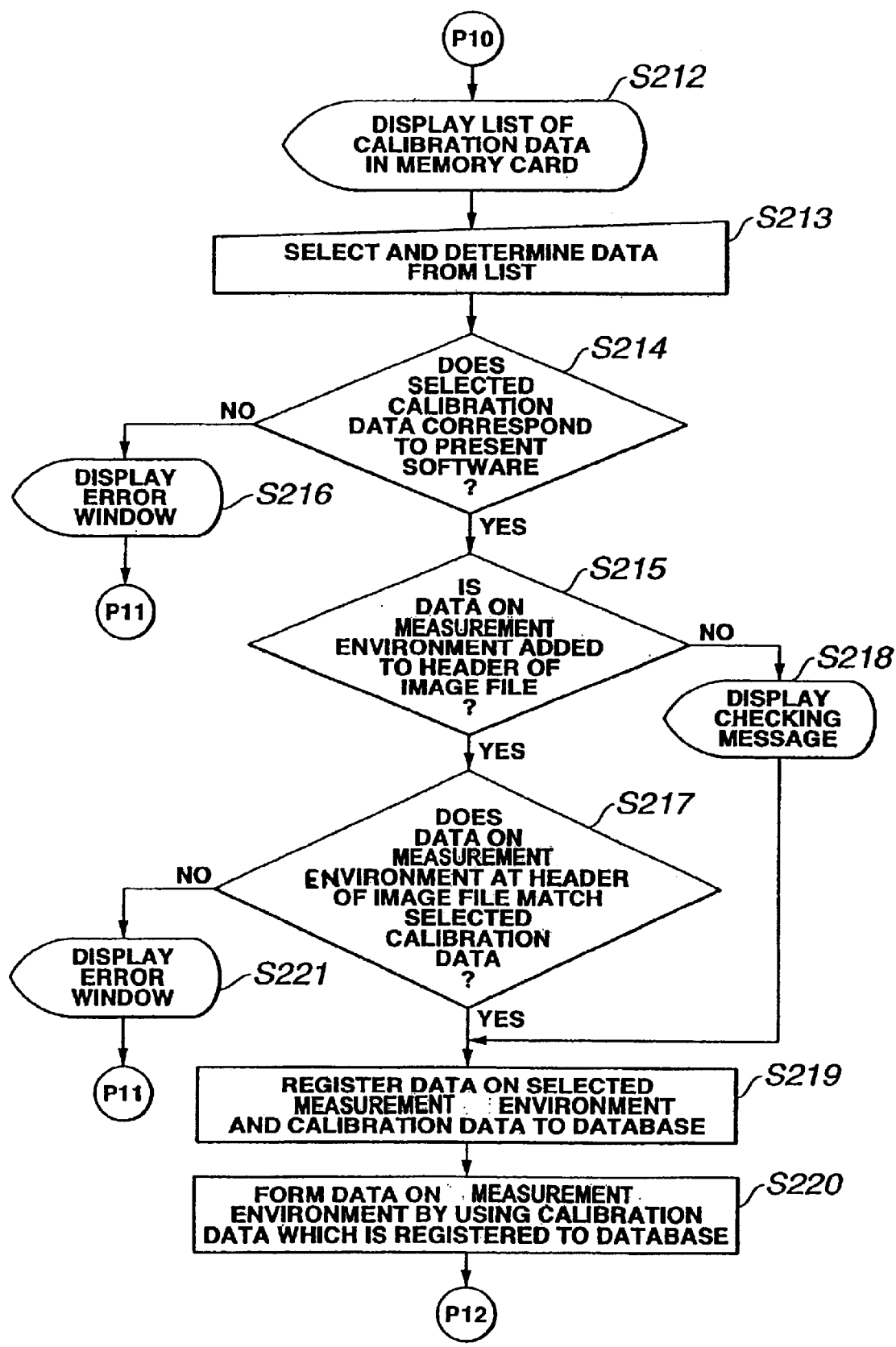
FIG. 23B is another part of the second flowchart showing the example of the control operation of the measurement software as the feature according to the fourth embodiment.

FIG. 19 is a diagram showing a display example of a thumbnail screen according to the fourth embodiment, FIG. 20 is a diagram showing a display example of a measurement screen of a stereo optical adaptor according to the fourth embodiment, FIG. 21 is a diagram showing a display example of the measurement screen of a normal optical adaptor according to the fourth embodiment, FIG. 22A is one part of a first flowchart showing an example of control operation of measurement software as a feature according to the fourth embodiment, FIG. 22B is another part of the first flowchart showing the example of the control operation of the measurement software as the feature according to the fourth embodiment, FIG. 23A is one part of a second flowchart showing the example of the control operation of measurement software as a feature according to the fourth embodiment, and FIG. 23B is another part of the second flowchart showing the example of the control operation of the measurement software as the feature according to the fourth embodiment.

According to the fourth embodiment, the system structure and the circuitry structure of the measurement endoscope apparatus are substantially the same as those according to the first embodiment. The fourth embodiment has the system structure and the circuitry structure shown in FIGS. 1 and 2. The stereo measurement adaptor used for the endoscope according to the fourth embodiment is the same as that shown in FIGS. 4 and 5 according to the first embodiment. Further, the normal optical adaptor used for the measurement endoscope apparatus according to the fourth embodiment is the same as that shown in FIGS. 10 and 11 according to the first embodiment.

According to the fourth embodiment, the measurement processing control is mainly different from that according to the first embodiment. Therefore, the same reference numerals denote the same components and different points are mainly described hereinbelow.

According to the fourth embodiment, the stereo measurement in the endoscope is performed by executing at least: first processing for reading optical information from the recording medium (such as the compact flash memory card) on which the optical data from the stereo optical adaptor 37 is recorded; second processing for reading the positional information between the image pick-up device 43 in the endoscope tip portion 39 and the stereo optical adaptor 37; third processing for obtaining a position error based on the above-mentioned positional information and main positional information between the endoscope and the stereo optical adaptor 37 obtained upon manufacturing; fourth processing for correcting the optical data based on the position error; fifth processing for coordinate-transforming an image to be subjected to the measurement based on the corrected optical data; and sixth processing for obtaining three-dimensional coordinates at an arbitrary point by matching two images based on the coordinate-transformed image.

The CPU 26 allows the stereo optical adaptor 37 to execute, for example, the first to fourth processing once, and controls the operation so that the processing results are recorded to the compact flash memory card 23 as data on the measurement environment. Upon executing the stereo measurement after that, the CPU 26 controls the operation for loading the data on the measurement environment to the RAM and then for executing the fifth to seventh processing.

The second processing for reading the positional information between the image pick-up device 43 in the endoscope tip portion 39 and the stereo optical adaptor 37 is performed by capturing the shape of the mask provided for the stereo optical adaptor and comparing the mask shape and the mask position upon manufacturing with the captured mask shape and mask position, as shown in FIG. 7. In this case, the mask shape is obtained by capturing a white image (e.g., reflecting a white sheet). The brightness of the white image in this case is determined depending on the gain of the CCU 25 and the shutter speed.

Ordinarily, the gain of the CCU 25 and the shutter speed of the image pick-up device 43 are automatically controlled so as to match the best condition. However, when capturing the mask shape, the gain of the CCU 25 is set to be low and the shutter speed of the image pick-up device 43 is set to be high and therefore the image is dark and the mask shape cannot clearly be photographed. This adversely influences the measurement accuracy. Thus, according to the fourth embodiment, the gain of the CCU 25 and the shutter speed are fixed under the control of the CPU 26. Accordingly, the mask shape can be captured without fail and lowering of the measurement precision is prevented.

After preparing the measurement, for example, when performing the measurement of the length of the crack 44 in FIG. 6, the measurement point is designated by a broken line to trace the crack 44 on the left image. The CPU 26 searches for a corresponding point on the right image upon every designation of a new measurement point, obtains three-dimensional coordinates at the measurement point based on coordinates of the measurement point and the corresponding point, calculates a distance between two adjacent points based on the three-dimensional coordinates, calculates the sum of the distances, and displays the entire length of the crack 44 on the LCD 14.

According to the fourth embodiment, the endoscope performs the measurement using the normal optical adaptor by utilizing a comparison measurement method, similarly to the case according to the first embodiment. Namely, the comparison measurement is performed by using a known dimension on the screen as a base.

For example, when a diameter of a circle shown in FIG. 12 is known, a pointer is placed at both ends of the diameter of the circle and the length La 45 between the two points is inputted. The length to be known Lb 46 is obtained by a ratio through calculation of the CPU 26 based on the size of the length La on the screen. In this case, distortion correction is executed based on information on distortion characteristics of the lens so as to obtain the dimension more accurately by adjustment. The distortion characteristics of the lens are previously recorded on the ROM 27, and the CPU 26 implements the comparison measurement so that data corresponding to the selected normal optical adaptor 42 is loaded to the RAM 2.

According to the fourth embodiment, in the endoscope, in order to store the setting of a plurality of stereo measurement adaptors, it is controlled that the data on the measurement environment is recorded to the detachable compact flash memory card 23.

The data on the measurement environment comprises the information on the measurement environment, the calibration data, the transform table, and the inverse transform table.

Since the information on the measurement environment includes the type of the data on the measurement environment, that is, the type of the calibration data or the type of the transform table, it includes the following information.

(a) The type of stereo measurement adaptor and the individual identification number (b) The type of the endoscope insertion portion and the individual identification number (c) TV type such as NTSC, (d) The type of CCU, and (e) The type of video capturing circuit Incidentally, since the type of CCU and the type of the video capturing circuit are provided as modules of the endoscope in many cases, they may be replaced with the type of the measurement endoscope in this case.

Further, the calibration data is obtained by correcting the optical data indicating the optical characteristics measured in the manufacturing step of the stereo measurement adaptor to information suitable to the measurement endoscope used for actual measurement. Therefore, the calibration data further includes the following contents.

(f) Positional information on the attachment of the combination of the endoscope used for data measurement in the manufacturing step and the optical adaptor, and positional information of the attachment of the combination of the endoscope used for actual measurement and the optical adaptor (g) A correction formula in which the correction for the positional shift is performed based on the two pieces of positional information on the attachment, to geometric-deformation correction formula of two optical systems which is obtained by the data measurement in the manufacturing step (h) Position coordinate of the optical axes in which the correction for the positional shift is performed based on the two pieces of positional information on the attachment, to position coordinate of the optical axes of the two lenses which is obtained by the data measurement in the manufacturing step (i) Distance of the optical axes in the two lens which is obtained by the data measurement in the manufacturing step (j) Focusing distance between the two lens systems which is obtained by the data measurement in the manufacturing step The transform table included in the data on the measurement environment is for the geometric deformation correction for the measurement image photographed by the present measurement endoscope by using the calibration data. The corrected image after correcting the deformation can be formed by using the transform table.

The inverse transform table included in the data on the measurement environment is for obtaining coordinates on the original image before correction to the coordinates on the corrected image.

Further, according to the fourth embodiment, in the measurement endoscope, the photographed image is recorded to the PCMCIA memory card 22 together with the calibration data and the information on the measurement environment used for measurement under the control operation of the CPU 26.

Furthermore, according to the fourth embodiment, the calibration data and the information on the measurement environment included in the selected one of a plurality of pieces of the data on the measurement environment registered in the present apparatus can be recorded to a detachable memory card different from the PCMCIA memory card 22 for recording the image and from the compact flash memory card for recording the data on the measurement environment.

According to the fourth embodiment, the measurement software is recorded to the PCMCIA memory card 22 by the above described endoscope, captures the measurement image with the calibration data and the information on the measurement environment on the PC, sets the same measurement environment as that of the endoscope upon photographing the image, and performs the same measurement on the PC. The measurement software is described hereinbelow.

According to the fourth embodiment, the PC related software performs the measurement by executing: first processing for capturing the image recorded by the above described endoscope to the PC and managing the captured image; second processing for selecting one of the managed images and calling the measurement function; third processing for managing the calibration data and the information on the measurement environment recorded to the recording medium in the PC; fourth processing for associating the calibration data suitable to the measurement image; fifth processing for forming the transform table for correcting the geometric deformation included in the image; sixth processing for coordinate-transforming the image photographed for measurement by using the transform table and forming the corrected image; seventh processing for matching two left and right images at an arbitrary point based on the corrected image; eighth processing for obtaining a three-dimensional coordinate based on the two left and right coordinates obtained by the matching, the position coordinates of the optical axes, and the focusing distance; and ninth processing for obtaining measurement values such as a distance between two points and an area based on the three-dimensional coordinates at a plurality of arbitrary points.

The memory card to which the measurement image is recorded is attached to the PC and the image is selected in the memory card by the present software. Then, in the first processing, the images are copied to a folder in the PC which are managed by the present software. After ending the first processing, a thumbnail 55 comprising the above-copied image is displayed on a thumbnail screen of the present software as shown in FIG. 19. When recording to the header of the copied image file, a sign indicating the image for stereo measurement or the image for comparison measurement, a stereo measurement icon 56 or a comparison measurement icon 57 is displayed on the thumbnail 55 in accordance with the recorded sign.

The image for measurement is selected on the thumbnail screen and a measurement executing menu (not shown) is selected from a menu bar 58. Further, a measurement executing button 60 is pressed from a tool bar 59, and, alternatively, the stereo measurement icon 56 or the comparison measurement icon 57 is pressed on the thumbnail. Thus, in the second processing, the measurement functions are called. After preparing the measurement, the screen becomes a stereo measurement screen as shown in FIG. 20 or a comparison measurement screen as shown in FIG. 21.

FIG. 20 shows an example for displaying various menu buttons 61 for executing the various measurement functions, a message display column 63 for displaying a message or the like of the operation, a various-value display column 62 for displaying the measurement result (numerical value), and two left and right measurement areas in the field of view 64 which are cut off from the measurement image and are pasted on the measurement screen.

FIG. 21 shows an example for displaying various menu buttons 61, a message display column 67, a various-value display column 66, and a measurement image 68.

In the measurement endoscope, a plurality of pieces of data on the measurement environment are registered. The total capacity of the transform table and the inverse transform table included in the data on the measurement environment is, e.g., 12 Mbytes. Therefore, three stereo measurement adaptors are registered in the present endoscope and the total capacity is 36 Mbytes (=12 Mbytes×3). The formation of the data on the measurement environment takes a long time under the limitation of the CPU, and various measurement is performed by using several types of optical adaptors in many cases. Thus, some pieces of the data on the measurement environment are previously formed to be recorded as much as possible within the capacity of the flash ROM or compact flash memory card provided for the endoscope.

On the contrary, the processing speed of the PCs which have recently been sold is faster than that of the endoscope by as much as several tens times. Consequently, the data on the measurement environment is formed on the PC and thus the complete formation of the data takes several to several tens seconds. Further, a large number of images are managed on the PC and various types of the data on the measurement environment need to be used. Therefore, by forming the data on the measurement environment based on the calibration data added to the image upon every selection of the image and execution of the measurement, it is sufficient to assure the capacity of one piece of the data on the measurement environment.

Further, the calibration data necessary for formation of the data on the measurement environment is excessively small, for example, several tens Kbytes. Therefore, a plurality of pieces of the calibration data can easily be stored in the PC and thus many measurement environments can be registered. If the calibration data is not added to the image, the suitable calibration data is selected from the list of the calibration data and, conveniently, the data on the measurement environment can be formed and the measurement can be performed.

Herein, a plurality of pieces of the data on the measurement environment and calibration data registered in the PC can easily be registered by the two following methods.

According to a first method, it is searched whether or not there is data on the measurement environment which has already been registered of the same measurement environment as that of the selected image upon selecting the information on the measurement environment and the measurement image with the calibration data and performing the measurement. When registering no data on the measurement environment of the same measurement environment as that of the selected image, the information on the measurement environment and the calibration data added to the image are automatically copied and registered in a folder which is managed by the present software.

According to a second method, the appropriate data on the measurement environment is selected from the data on the measurement environment which has been registered, and the detachable recording medium to which the information on the measurement environment and the calibration data have been recorded is previously prepared. Alternatively, the appropriate measurement environment which has been registered on the present software is selected and the detachable recording medium to which the information on the measurement environment and the calibration data have been recorded is previously prepared. The above-prepared recording medium is attached to the PC, the appropriate information on the measurement environment and calibration data which have been recorded to the present software are selected, and the selected data is copied and registered to the folder managed by the present software.

As mentioned above, it is possible to easily set the measurement environment with any measurement image which is recorded by various measurement environment apparatuses and to perform the re-measurement promptly under the measurement environment corresponding to the present software.

Next, a detailed description is given of the control operation of the software as a feature according to the fourth embodiment with reference to FIGS. 22A, 22B, 23A, and 23B.

The present software captures the measurement image which is recorded by the endoscope. One appropriate thumbnail is selected on the screen in FIG. 19 by the mouse or key operation. A routine program shown in FIGS. 22A and 22B is executed by selecting the measurement executing menu in the menu bar 58, pressing the measurement executing button 60 from the tool bar 59, and pressing the stereo measurement icon 56 or the comparison measurement icon 57 on the thumbnail.

Upon executing the routine shown in FIGS. 22A and 22B, in step S111, it is determined whether or not the image is recorded by the endoscope by referring to the header of the selected image file. If the image is recorded by the measurement endoscope apparatus, in determination processing in step S112, it is determined whether or not the image is the stereo measurement image by referring to the header of the image.

If the image is the stereo measurement image, in step S113, it is determined whether or not the information on the measurement environment is added to the header of the image file. If the information on the measurement environment is recorded, in step S114, it is determined whether or not the present software corresponds to the calibration data recorded to the image. If the calibration data corresponds to the present software, the processing routine proceeds to processing in step S116. If the calibration data recorded in the image does not correspond to the present software in the determination processing in step S114, the fact that the stereo measurement is impossible is displayed and the screen returns to the screen in FIG. 19 so as to select another image.

In determination processing in step S116, it is determined whether or not there is the same information on the measurement environment as that of the image in the data on the measurement environment recorded to the measurement environment database which has already been registered in the PC. If there is the same information on the measurement environment, the processing routine proceeds to step S118. If there is no data on the measurement environment in the determination processing in step S116, the information on the measurement environment and the calibration data added to the image are registered in the database and then the processing routine proceeds to step S118.

In determination processing in step S118, it is determined whether or not the information on the measurement environment is the same as that of the data on the measurement environment which has already been formed and set. If the information on the measurement environment is the same, in step S119, it is determined whether or not the difference between the positional information in the area in the field of view included in the calibration data added to the image and the positional information in the area in the field of view included in the current data on the measurement environment is smaller than a predetermined threshold.

If it is determined in the processing in step S119 that the difference is smaller than the threshold, the currently-set data on the measurement environment is read and the stereo measurement processing is executed in step S121.

If the information on the measurement environment is not the same in step S118 and if the difference is larger than the threshold in the determination processing in step S119, the data on the measurement environment is newly formed by using the calibration data added to the header of the image file and the stereo measurement processing is executed in step S121.

The preparation for stereo measurement is completed in step S121 and then the apparatus enters the standby mode on the screen in FIG. 20. The measurement is performed on the screen and the stereo measurement result is displayed.

After closing the screen, the apparatus returns to the screen in FIG. 19 so as to select another image.

If the information on the measurement environment and the calibration data are not added to the measurement image in step S113, the data on the measurement environment suitable to the image is manually selected so that the apparatus enters the standby mode of the measurement. Then, in step S123, the routine program shown in FIGS. 23A and 23B in executed.

That is, in step S201, the user selects the use of the appropriate calibration data which has already been registered, the use of the calibration data which is recorded to another recording medium, or the end of the measurement.

If selecting the appropriate calibration data which has already been registered, in step S203, the list of the calibration data registered in the measurement environment database is displayed. In step S204, the user selects the appropriate calibration data. Subsequently, in step S205, it is determined whether or not the information on the measurement environment is added to the image. If the information on the measurement environment is added, in step S206, it is determined whether or not the contents of the information on the measurement environment recorded to the image file match the contents of the information on the measurement environment of the calibration data selected by the user. If matching in step S206, the processing routine proceeds to step S209.

If the contents of the information in the image file does not match the contents of the information of the selected calibration data in step S206, a fact reflecting that the selected calibration data is unavailable, the processing routine returns to step S201, whereupon another calibration data is selected.

If the information on the measurement environment is not added to the image in step S205, the contents of the information on the measurement environment in the selected calibration data is confirmed by the user and the processing routine proceeds to step S209.

In step S209, the data on the measurement environment is formed by using the calibration data selected from the list and the stereo measurement processing is executed.

If the data from the database is not used and the calibration data recorded to another recording medium is used in step S201, the recording medium to which the calibration data is recorded is inserted into the PC. Then, in step S212 in FIG. 23B, the list of the calibration data in the PC is displayed.

After selecting the appropriate calibration data from the list by the user, it is determined whether or not the calibration data selected in the determination processing in step S214 corresponds to the present software. If the selected calibration data in step S214 corresponds to the present software, it is determined in step S215 whether or not the information on the measurement environment is recorded to the image. If the information on the measurement environment is recorded to the image, in determination processing in step S217, it is determined whether or not the contents of the information on the measurement environment recorded to the image file corresponds to the contents of the information on the measurement environment of the calibration data selected by the user. If the contents of the information on the measurement environment recorded to the image file matches the contents of the information on the measurement environment of the selected calibration data in step S217, the processing routine proceeds to step S219.

If the information on the measurement environment is not recorded to the image in step S215, the user confirms the contents of the information on the measurement environment in the selected calibration data again and the processing routine proceeds to step S219.

The calibration data and information on the measurement environment selected in step S219 are registered to the database, the data on the measurement environment is formed by using the calibration data in step S220, and the stereo measurement processing is executed.

On the other hand, if the calibration data selected in step S214 does not correspond to the present software and if the contents of the information on the measurement environment in the image do not match the contents of the information on the measurement environment of the selected calibration data in step S217, a fact that the selected calibration data is unavailable is displayed and the processing routine returns to step S201 in FIG. 23A whereupon another calibration data is selected.

After the processing in step S209 and step S220 is completed, the information on the measurement environment and the calibration data may be recorded to the header to the image file in accordance with the user's desire before executing the stereo measurement.

Further, if the image selected in step S112 in FIG. 22A is not the image for the stereo measurement, in step S124 in FIG. 22B, it is determined whether or not the image is obtained by the comparison measurement by referring to the header of the image. If the image is obtained by the comparison measurement, in step S125, the information for correcting the deformation of the optical adaptor recorded to the image is read and the comparison measurement processing is executed.

On the other hand, if the selected image is neither the stereo measurement image nor the comparison measurement image in the determination processing in step S124, the screen returns to the screen in FIG. 11 on which the measurement processing ends and another image is selected. Alternatively, in step S127, the user selects the measurement method.

If the selected measurement method is the comparison measurement in step S127, the information for correcting the deformation of the initial value is read and the comparison measurement processing is executed.

If the stereo measurement is selected in step S127, the processing routine proceeds to step S123 whereupon the program shown in FIGS. 23A and 23B is executed and the appropriate calibration data is selected from the list so as to perform the measurement.

If the image selected in step S111 is not the image recorded by the measurement endoscope apparatus and if the measurement ends in step S128, the screen returns to the screen in FIG. 19 and the apparatus enters the standby mode so as to select another image.

According to the fourth embodiment, as mentioned above, only by selecting the measurement image and executing the measurement, the correct information necessary for measurement is read and the measurement environment is set. Thus, the correct measurement can be performed not only on the endoscope but also on general PCs.

Further, solely by selecting the measurement image and pressing the measurement executing menu or the measurement button irrespective of the type of measurement, the appropriate measurement program is executed.

Furthermore, when performing the measurement by using the image with the information on the measurement environment and the calibration data and when the information on the measurement environment indicating the type of the used device upon photographing the image matches the current setting, the measurement is performed by using the current setting. Then, the photographing status of the white image to be photographed for examining the position in the area in the field of view changes due to some reason. The measurement precision is decreased due to the change in the information on the positional relationship in accordance therewith.

According to the fourth embodiment, when the information on the measurement environment indicating the type of the used device upon photographing the image matches the current setting, it is confirmed whether or not the positional information in the area in the field of view is changed. Thus, not only the number of cases that decrease the precision due to the above-mentioned reason are reduced, but also the measurement environment is automatically set by using the calibration data which has been registered in the image. Thus, the safety is improved and the preparation for the measurement can be performed promptly and easily.

Since the capacity of the calibration data is several tens Kbytes and the information on the measurement environment is several Kbytes in many cases, only the information on the measurement environment is recorded to the image so as to reduce one image file.

Further, when the information on the measurement environment and the calibration data are recorded to a file different from the image file, it is considered that the file of the information on the measurement environment and calibration data which have been recorded in association with the image is lost or deleted due to some reason.

In conventional endoscope systems, the re-measurement cannot be performed on the apparatus with the above-mentioned image and, alternatively, the setting of the measurement environment until the actual re-measurement is completed.

On the other hand, according to the fourth embodiment, solely by selecting the data on the measurement environment from the list thereof which has already been registered and the calibration data which is recorded to another memory card, the measurement environment can easily be set on the PC and the re-measurement can promptly be performed.

Further, since it is confirmed whether the data selected from the list matches the image for measurement, advantageously, the number of cases in which the measurement is performed in the mismatched status is reduced.

According to the fourth embodiment, it is possible to perform the re-measurement for the image recorded to the detachable recording medium in the endoscope by setting the measurement environment on the PC. In this case, it is possible to prevent the execution of the measurement by using the image which is not an image for measurement. The user can easily execute the measurement corresponding to the correct optical adaptor without paying attention to the type of optical adaptors. Thus, the operability upon re-measurement is improved and the examining efficiency is improved.

The endoscope adapts to various measurement environments. Further, the data on the measurement environment is formed again according to necessity and, therefore, only the capacity of a set of the data on the measurement environment may be ensured in the recording medium (HD) in the PC. Thus, the specification of the HD in the PC is not particularly limited.

When executing the measurement with the measurement image with the first type of the calibration data, the measurement image can automatically be captured in the managed calibration data. The user can perform the re-measurement without recognizing the presence of the calibration data.

Since only the calibration data can be recorded to the recording medium separately from the measurement image or be captured in the PC, the re-measurement can be performed by using the image without the calibration data.

Further, since the re-measurement is not necessary on the apparatus in which the image is actually photographed, the recording medium to which the image is recorded is attached to another apparatus and the re-measurement can be performed on another apparatus with simple operation.

Consequently, the status of the environment in various endoscopes can be read on the single PC. Thus, the measurement image can be subjected to easy re-measurement on the PC which is conveniently used by the current user. In addition, a plurality of users can easily share the image or the data on the measurement result by using a network system of the computer. The examining environment is thus exceedingly improved.

That is, according to the fourth embodiment, the measurement image is captured to the PC together with the information on the measurement environment and the calibration data. A proper image is selected from a plurality of stored images and the stereo measurement function is executed. Thereby, the measurement environment is automatically set from the information on the measurement environment and calibration data which are recorded to the measurement image. Thus, the measurement processing can be executed on the PC promptly. In this case, the information on the measurement environment and the calibration data added to the image are automatically copied to the database of the calibration data and are managed separately from the image.

The endoscope system which is highly adaptable to the measurement environment comprises means for searching the same calibration data which has already been managed in the PC by referring to the information on the measurement environment which is recorded to the measurement image and means for automatically changing the measurement environment by using the data as the search result. Thus, when executing the measurement by using the image without the calibration data for reason of the capacity of the medium for recording the image, if the data on the measurement environment is the same as the measurement information as the selected image in the endoscope, the data on the measurement environment is automatically formed from the calibration data which already exists. The measurement processing can be executed by using the formed data.

Further, the endoscope comprises means for determining that the setting of the measurement environment matches that of the current measurement environment by referring to the information on the measurement environment which has been recorded to the measurement image. Thus, the measurement processing can be performed by using the data on the measurement environment which is currently set, without additionally forming the data on the measurement environment. The time for preparing the measurement is greatly reduced.

Furthermore, even if neither the information on the measurement environment nor the calibration data is recorded to the measurement image for some reason, the measurement technician can perform the measurements without recognizing whether or not the measurement environment of the selected image is recorded because the endoscope comprises means for indicating that neither the information nor the data is recorded. In this case, the list of the calibration data which has already existed in the PC is displayed and the proper calibration data is selected, thus performing the measurement.

In addition to writing of the image to the recording medium or capturing the image from the recording medium, the calibration data in the PC can be copied to the recording medium and the calibration data in the recording medium can be captured in the database in the PC. Therefore, a database in which only the calibration data is independently managed can be provided. Consequently, in the case of the re-measurement by using the image without the calibration data and the data on the measurement environment, the proper calibration data is captured in the database via the recording medium and the re-measurement can easily be performed with the above-mentioned image.

As mentioned above, in the present invention, it is possible to prevent the taking of measurements under an erroneous measurement environment in the case of re-measurement using the recorded measurement image. Advantageously, by performing the re-measurement with the simple operation under the correct measurement environment, the re-measurement can promptly be performed without recognizing the measurement environment and the operability in this case is improved. Further, advantageously, the measurement image recorded on the endoscope is subjected to the re-measurement on the PC and thus the examination efficiency is improved.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A measurement endoscope system, comprising:
   an endoscope tip portion and a connecting portion;
   an image pick-up and;
   an optical adaptor detachably connectable to said connecting portion, for coupling a subject image to said image pick-up;
   a signal processing unit for processing an image signal from said image pick-up;
   a recording device for recording an image processed by said signal processing unit; and
   measurement means for performing measurements based on said image;
   wherein said measurement endoscope system further comprises:
   measurement environment data recording means for recording first data on a measurement environment as a pair of image data related to the image recorded by said recording device;
   comparing means for comparing said first data with second data which has already been recorded to said system; and
   selecting means for selecting said first data or said second data in accordance with information provided by said comparing means.

2. A system according to claim 1, further comprising:
   forming means for forming said first data also based on calibration data.

3. A system according to claim 2, further comprising:
   positional information determining means for determining an amount of positional shift from a predetermined value based on information on a positional relationship to a given endoscope,
   wherein said calibration data includes said information on the positional relationship.

4. An endoscope system, comprising:
   an endoscope tip portion and a connecting portion;
   an image pick-up for forming a measurement image, and;
   a plurality of types of optical adaptors detachably connectable to said connecting portion, for coupling a subject image to said image pick-up;
   processing means for measuring an image signal from said image pick-up by imaging processing through connecting one of said optical adaptors;
   means for storing and managing a plurality of pieces of data on the measurement environment which are formed by setting a measurement environment by using said plurality of optical adaptors;
   means for displaying said plurality of pieces of the data on the measurement environment;
   means for selecting the data on the measurement environment from said display means and performing measurement processing;
   means for recording the measurement image to a detachable recording medium; and
   means for selecting the measurement image which has already been recorded and executing the measurement processing;
   wherein said endoscope system further comprises:
   means for recording information on the measurement environment indicating the type of device used upon photographing a subject to obtain the measurement image;
   means for recording calibration data including optical characteristics of the optical adaptor for setting the measurement environment to the measurement image;
   means for copying to the detachable recording medium, the measurement image recorded in said system together with the information on the measurement environment and the calibration data;
   means for capturing the image copied to the recording medium in said system together with the information on the measurement environment and the calibration data;
   means for obtaining a search result by searching the same information on the measurement environment from data already obtained by referring to the information on the measurement environment recorded as part of the measurement image;

means for automatically changing the setting of the measurement environment by using the data obtained as said search result;

means for automatically setting the measurement environment by using the calibration data; and;

means for indicating that the information on the measurement environment and the calibration data are not recorded to the measurement image.

5. An endoscope system according to claim 4, further comprising:

means for storing and managing a plurality of pieces of the calibration data;

means for taking out only the calibration data which is recorded about the measurement image to said managing means and automatically capturing the calibration data together with the information on the measurement environment;

means for copying the data selected from the plurality of pieces of the calibration data to the recording medium;

means for capturing the calibration data copied to the recording medium to the system; and means for setting the measurement environment by using the data selected from the plurality of pieces of the calibration data.

6. An endoscope system according to claim 4 or 5, wherein the information on the measurement environment is effective to distinguish from the plurality of pieces of the calibration data.

7. An endoscope system according to claim 4 or 5, wherein sufficient for forming the data on the measurement environment, by setting the measurement environment or the data on the measurement environment which is formed by setting the measurement environment and which is ultimately used for measurement.

8. An endoscope system according to claim 4, wherein the information on the measurement environment and the calibration data are written to an image file or are recorded to a different file associated with the image file.

9. A measurement system comprising:

an endoscope;

a connecting portion provided for a tip portion of said endoscope;

an image pick-up and an optical adaptor detachably connectable to said connecting portion, for coupling a subject image to said image pick-up;

a signal processing unit for processing an image signal from said image pick-up;

recording means for recording an image processed by said signal processing unit;

measuring means for performing measurements based on the image;

first measurement environment data recording means for recording first data on a measurement environment as a pair of image data related to the image recorded by said recording means;

second measurement environment data recording means for recording second data on the measurement environment;

comparing means for comparing said first data with said second data which has previously been recorded; and selecting means for selecting said first data or said second data in accordance with information from said comparing means.

10. A measurement system according to claim 9, further comprising:

forming means for forming said first data from the data on the measurement environment and from calibration data.

11. A measurement system according to claim 10, further comprising:

positional information determining means for determining an amount of shift from a predetermined value based on information on a positional relationship to said endoscope, wherein said calibration data includes said information on the positional relationship.

12. A measurement system comprising:

an endoscope;

a connecting portion provided for a tip portion of said endoscope;

an image pick-up for forming a measurement image and a plurality of types of optical adaptors detachable to said connecting portion, for coupling a subject image to said image pickup;

processing means for performing measurement of an image signal from said image pickup by imaging processing which includes connecting one of said optical adaptors;

means for storing and managing a plurality of pieces of data on a measurement environment, said pieces of data being formed by setting the measurement environment by using said plurality of optical adaptors;

means for displaying said plurality of pieces of the data on the measurement environment;

means for selecting the data on the measurement environment from said display means and performing measurement processing;

means for recording the measurement image to a detachably connectable recording medium;

means for selecting the measurement image which has already been recorded to the recording medium and executing the measurement processing;

means for recording information on the measurement environment indicating the type of a device used in photographing a subject for the measurement image;

means for recording calibration data including optical characteristics of the optical adaptor, that is sufficient to associate the measurement environment to the measurement image;

means for copying to the recording medium, the measurement image together with the information on the measurement environment and the calibration data;

means for capturing the image copied to the recording medium in said system together with the information on the measurement environment and the calibration data;

means for searching the same information on the measurement environment from data which has already been managed in said system by referring to the information on the measurement environment which is recorded to the measurement image to produce a search result;

means for automatically changing the setting of the measurement environment by using the search result;

means for automatically setting the measurement environment by using the calibration data recorded to the measurement image; and means for indicating that the information on the measurement environment and the calibration data are not recorded to the measurement image.

13. A measurement system according to claim 12, further comprising:
   means for storing and managing a plurality of pieces of the calibration data;
   means for taking out only the calibration data which is recorded about the measurement image to said managing means and automatically capturing the calibration data together with the information on the measurement environment;
   means for copying the data selected from the plurality of pieces of the calibration data to the recording medium;
   means for capturing the calibration data copied to the recording medium to said system; and
   means for setting the measurement environment by using the data selected from the plurality of pieces of calibration data.

14. A measurement apparatus according to claim 12 or 13, wherein the information on the measurement environment is information that is effective for distinguishing from the plurality of pieces of the calibration data.

15. A measurement apparatus according to claim 12 or 13, wherein the calibration data includes a correction coefficient of the optical characteristics, which comprises sufficient data for forming the data on the measurement environment formed by setting the measurement environment or the data on the measurement environment which is formed by setting the measurement environment and which is finally used for measurement.

16. A measurement system according to claim 12, wherein the information on the measurement environment and the calibration data are written to an image file or are recorded to a different file associated with the image file.

17. A measurement processing method usable with a personal computer for capturing a measurement image recorded by an environment measuring apparatus and copying the captured image, said environment measuring apparatus comprising: a connecting portion provided for an endoscope tip portion; an optical adaptor detachably connected to said connecting portion which includes an objective lens, for coupling two images to image pick-up means; processing means for performing measurement of an image signal from said image pick-up means by imaging processing by connecting said optical adaptor; means for recording to a measurement image, calibration data including optical characteristics of said optical adaptor, as information necessary for setting the measurement environment; and
   means for copying the measurement image recorded in said apparatus to a recording medium together with the information on the measurement environment and the calibration data, said method comprising:
   a step of determining whether the information on the measurement environment matches a current setting of the measurement environment by referring to the information on the measurement environment recorded to the measurement image;
   a step of automatically setting the measurement environment by using the calibration data which is recorded to the measurement image;
   a step of managing a plurality of types of the calibration data taken out from the image in said personal computer;
   a step of searching the same information on the measurement environment from the calibration data which has already been managed in the personal computer by referring to the information on the measurement environment which is recorded to the measurement image to produce a search result;
   a step of automatically forming data on the measurement environment which is used upon correcting the deformation of the measurement image by using the calibration data as the search result;
   a step of forming the data on the measurement environment by using the data selected from the pieces of the calibration data;
   a step of coordinate-transforming the measurement image by using the data on the measurement environment;
   a step of obtaining a three-dimensional coordinate at an arbitrary point by matching two images based on the two coordinate-transformed images; and
   a step of calculating a measurement value from a parameter such as a desired length from said three-dimensional coordinate.

18. A measurement processing method according to claim 17, further comprising:
   a step of recording to the measurement image, the calibration data and the information on the measurement environment including optical characteristics of said optical adaptor, necessary for setting the measurement environment;
   a step of copying the measurement image copied to the PC to the recording medium to ether with the information on the measurement environment and the calibration data;
   a step of copying to the recording medium, only the information on the measurement environment and the calibration data which are managed in the personal computer, separately from the image; and
   a step of capturing the information on the measurement environment and the calibration data copied to the recording medium to the personal computer.

19. A measurement processing method according to claim 17 or 18, wherein the information on the measurement environment is information sufficient for distinguishing from the plurality of pieces of the calibration data.

20. A measurement processing method according to claim 17 or 18, wherein the calibration data includes a correction coefficient of the optical characteristics, and is the entire data necessary for forming the data on the measurement environment formed by setting the measurement environment or the data on the measurement environment which is formed by setting the measurement environment and which is finally used for measurement.

21. A measurement processing method according to claim 17, wherein the information on the measurement environment and the calibration data to be recorded to the image are written to an image file or are recorded to a different file associated with the image file.

22. A measurement processing method utilizing a personal computer for capturing a measurement image recorded by a environment measurement apparatus which processes the captured image, said measurement environment apparatus comprising: a connecting portion provided for an endoscope tip portion; an optical adaptor detachably connected to said connecting portion having an objective lens, for coupling two images to image pick-up means; processing means for performing measurement of an image signal from said image pick-up means by imaging processing by connecting said optical adaptor; means for recording to a measurement image, calibration data including optical characteristics of said optical adaptor, as information necessary for setting the measurement environment; and means for copying the measurement image recorded in said apparatus to a recording medium together with the information on the measurement environment and the calibration data, said method comprising:

a step of determining whether the information on the measurement environment matches a current setting of the measurement environment by referring to information on the measurement environment recorded to the measurement image;

a step of automatically setting the measurement environment by using the calibration data which is recorded to the measurement image;

a step of indicating that neither the information on the measurement environment nor the calibration data is recorded to the measurement image;

a step of managing a plurality of types of the calibration data taken out from the image in said personal computer;

a step of searching the same information on the measurement environment from the calibration data which has already been managed in the personal computer by referring to the information on the measurement environment which is recorded to the measurement image to create a search result;

a step of automatically forming the data on the measurement environment which is used upon correcting skewing of the measurement image by using the calibration data as the search result;

a step of forming the data on the measurement environment by using the data selected from pieces of the calibration data;

a step of coordinate-transforming the measurement image by using the data on the measurement environment;

a step of obtaining a three-dimensional coordinate at an arbitrary point by matching two images based the two coordinate-transformed images; and a step of calculating a measurement value based on a given parameter from said three-dimensional coordinate.

* * * * *

UNITED STATES PATENT AND TRADEMARK OFFICE
CERTIFICATE OF CORRECTION

PATENT NO.       : 6,945,930 B2  
APPLICATION NO.  : 10/232422  
DATED            : September 20, 2005  
INVENTOR(S)      : Yokota Page 1 of 1

It is certified that error appears in the above-identified patent and that said Letters Patent is hereby corrected as shown below:

In claim 7, column 35, line 31 after "wherein" insert --the calibration data includes a correction coefficient of optical characteristics, which is alone--.

Signed and Sealed this

Twelfth Day of September, 2006

JON W. DUDAS  
*Director of the United States Patent and Trademark Office*